(12) United States Patent
Bersano-Begey et al.

(10) Patent No.: US 8,951,484 B2
(45) Date of Patent: Feb. 10, 2015

(54) CIRCULATING TUMOR CELL CAPTURING TECHNIQUES AND DEVICES

(71) Applicant: The Regents of the University of Michigan, Ann Arbor, MI (US)

(72) Inventors: Tommaso F. Bersano-Begey, Ann Arbor, MI (US); Daniel F. Hayes, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 13/756,121

(22) Filed: Jan. 31, 2013

(65) Prior Publication Data

US 2013/0309707 A1   Nov. 21, 2013

Related U.S. Application Data

(60) Provisional application No. 61/593,092, filed on Jan. 31, 2012.

(51) Int. Cl.
*G01N 1/34* (2006.01)
*B01L 3/00* (2006.01)
(Continued)

(52) U.S. Cl.
CPC . *G01N 1/34* (2013.01); *B01L 3/502* (2013.01); *G01N 33/5091* (2013.01); *G01N 33/54366* (2013.01); *G01N 1/4077* (2013.01); *A61B 5/1427* (2013.01); *A61B 5/15003* (2013.01); *A61B 5/150229* (2013.01);
(Continued)

(58) Field of Classification Search
None
See application file for complete search history.

(56) References Cited

U.S. PATENT DOCUMENTS

| | | |
|---|---|---|
| 2006/0160243 A1 | 7/2006 | Tang et al. |
| 2007/0026469 A1 | 2/2007 | Fuchs et al. |

(Continued)

FOREIGN PATENT DOCUMENTS

| | | |
|---|---|---|
| WO | WO-03/085379 A2 | 10/2003 |
| WO | WO-2006/108087 A2 | 10/2006 |

(Continued)

OTHER PUBLICATIONS

Attard et al., Selective inhibition of CYP17 with abiraterone acetate is highly active in the treatment of castration-resistant prostate cancer, J. Clin. Oncol., 27(23):3742-8 (2009).

(Continued)

*Primary Examiner* — Jill Warden
*Assistant Examiner* — Timothy G Kingan
(74) *Attorney, Agent, or Firm* — Marshall, Gerstein & Borun LLP

(57) ABSTRACT

Candidate cells, such as circulating tumor cells (CTCs), present with blood are captured using a multiple stage device, having successive stages configured to deviate candidate cells out of the blood while slowing down the flow rates of the deviated resultant for easier capture of CTCs through progressive stages. The devices can include separation channel and deviation channels formed of micro-post patterns dimensioned to deviate different desired candidate cells for analysis.

25 Claims, 18 Drawing Sheets
(3 of 18 Drawing Sheet(s) Filed in Color)

(51) Int. Cl.
- *G01N 33/50* (2006.01)
- *G01N 33/543* (2006.01)
- *G01N 1/40* (2006.01)
- *A61B 5/155* (2006.01)
- *A61B 5/15* (2006.01)

(52) U.S. Cl.
CPC .......... *A61B 5/150755* (2013.01); *A61B 5/155* (2013.01); *B01L 2200/0647* (2013.01); *B01L 2300/087* (2013.01); *B01L 2300/0877* (2013.01)
USPC ............ 422/534; 422/50; 422/503; 422/552; 435/6.19; 435/7.21; 435/7.23; 435/287.1; 435/287.2; 435/283.1; 435/288.5; 435/305.2; 435/2; 604/5.01; 604/5.02; 604/6.09

(56) References Cited

U.S. PATENT DOCUMENTS

| | | | |
|---|---|---|---|
| 2008/0318324 | A1 | 12/2008 | Chiu et al. |
| 2010/0140171 | A1 | 6/2010 | Heath et al. |
| 2010/0197507 | A1 | 8/2010 | Rothberg et al. |
| 2010/0233694 | A1* | 9/2010 | Kopf-Sill ........................ 435/6 |
| 2010/0323388 | A1 | 12/2010 | Chiu et al. |
| 2011/0104718 | A1 | 5/2011 | Rao et al. |
| 2011/0244443 | A1* | 10/2011 | van Rijn et al. .................. 435/2 |

FOREIGN PATENT DOCUMENTS

| | | |
|---|---|---|
| WO | WO-2008/016414 A2 | 2/2008 |
| WO | WO-2009/051734 A1 | 4/2009 |

OTHER PUBLICATIONS

Bauernhofer et al., Association of disease progression and poor overall survival with detection of circulating tumor cells in peripheral blood of patients with metastatic breast cancer, Oncol. Rep., 13(2):179-84 (2005).

Chang et al., Biomimetic technique for adhesion-based collection and separation of cells in a microfluidic channel, Lab Chip, 5(1):64-73 (2005).

Cristofanilli et al., Circulating tumor cells, disease progression, and survival in metastatic breast cancer, N. Engl. J. Med., 351(8):351(8):781-91 (2004).

Davis et al., Deterministic hydrodynamics: taking blood apart, Proc. Natl. Acad. Sci. USA, 103(40):14779-84 (2006).

Desitter et al., A new device for rapid isolation by size and characterization of rare circulating tumor cells, Anticancer Res., 31(2):427-41 (2011).

Hong et al., Integrated nanoliter systems, Nat. Biotechnol., 21910):1179-83 (2003).

Huang et al., Continuous particle separation through deterministic lateral displacement, Science, 304(5673):987-90 (2004).

International search report and written opinion from PCT/US2013/024150 dated Apr. 8, 2013.

Kahn et al., Enumeration of circulating tumor cells in the blood of breast cancer patients after filtration enrichment: correlation with disease stage, Breast Cancer Res. Treat., 86(3):237-47 (2004).

Kim et al., Tumor self-seeding by circulating cancer cells, Cell, 139(7):1315-26 (2009).

Miller et al., Significance of Circulating Tumor Cells Detected by the CellSearch System in Patients with Metastatic Breast Colorectal and Prostate Cancer, J. Oncol., 2010:617421 (2010).

Nagrath et al., Isolation of rare circulating tumour cells in cancer patients by microchip technology, Nature, 450(7173):1235-9 (2007).

Nishimura et al., Label-free continuous cell sorter with specifically adhesive oblique micro-grooves, J. Micromechanics and Microengineering, 19(12):125002 (2009).

Pinzani et al., Isolation by size of epithelial tumor cells in peripheral blood of patients with breast cancer: correlation with real-time reverse transcriptase-polymerase chain reaction results and feasibility of molecular analysis by laser microdissection, Hum. Pathol., 37(6):711-8 (2006).

Stott et al., Isolation of circulating tumor cells using a microvortex-generating herringbone-chip, Proc. Natl. Acad. Sci. USA, 107(43):18392-7 (2010).

Vona et al., Variability of the CD4 and F13A1 short tandem repeats in Corsicans, Sardinians and Piaroa Indians, Gene Geogr., 10(1):51-63 (1996).

Whitesides, The origins and the future of microfluidics, Nature, 442(7101):368-73 (2006).

Wong et al., Prognostic significance of circulating tumour cells enumerated after filtration enrichment in early and metastatic breast cancer patients, Breast Cancer Res. Treat., 99(1):63-9 (2006).

Zheng et al., Membrane microfilter device for selective capture, electrolysis and genomic analysis of human circulating tumor cells, J. Chromatogr. A, 1162(2):154-61 (2007).

International Preliminary Report on Patentability, corresponding International Application No. PCT/US2013/024150, dated Aug. 5, 2014.

* cited by examiner

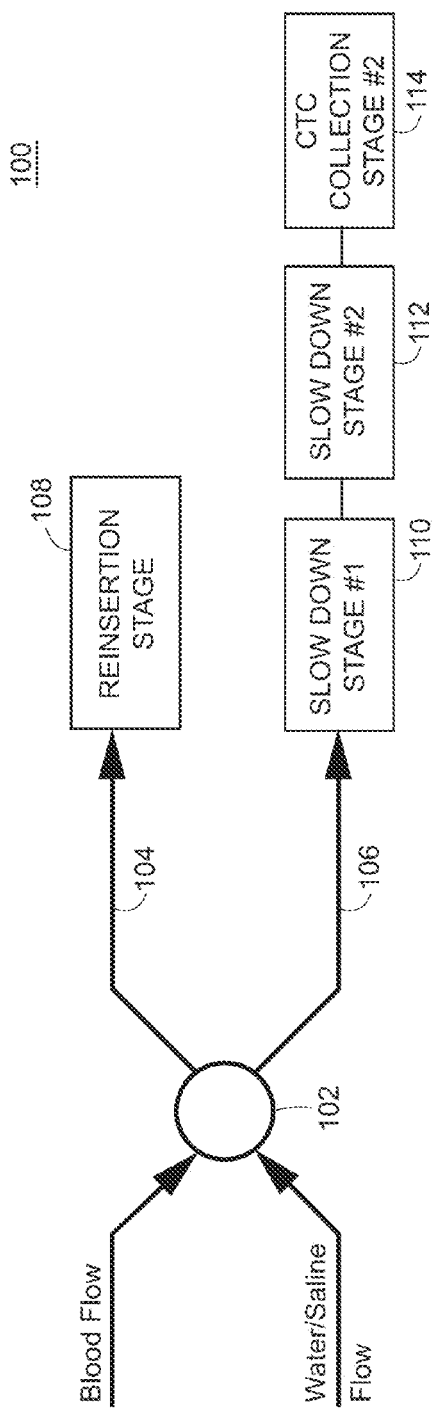
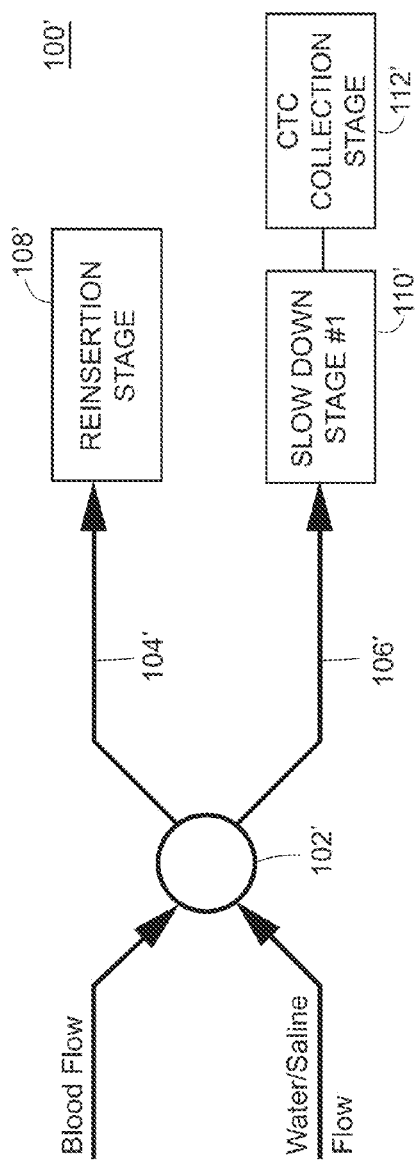

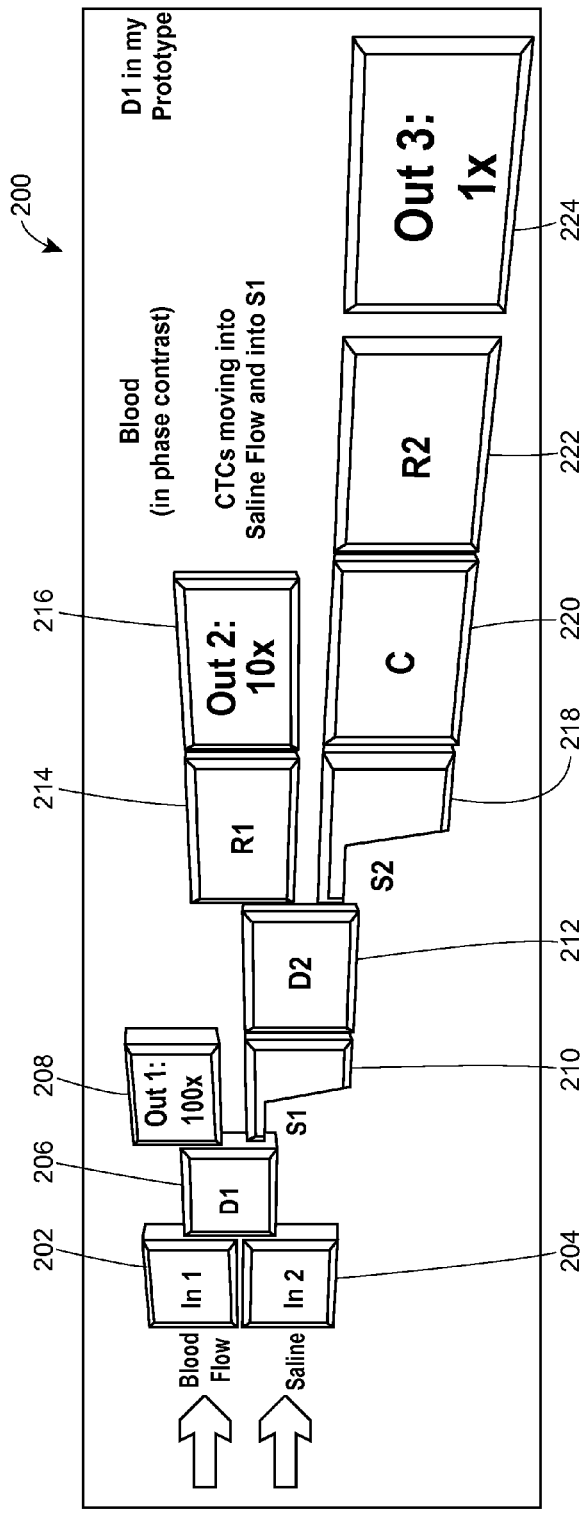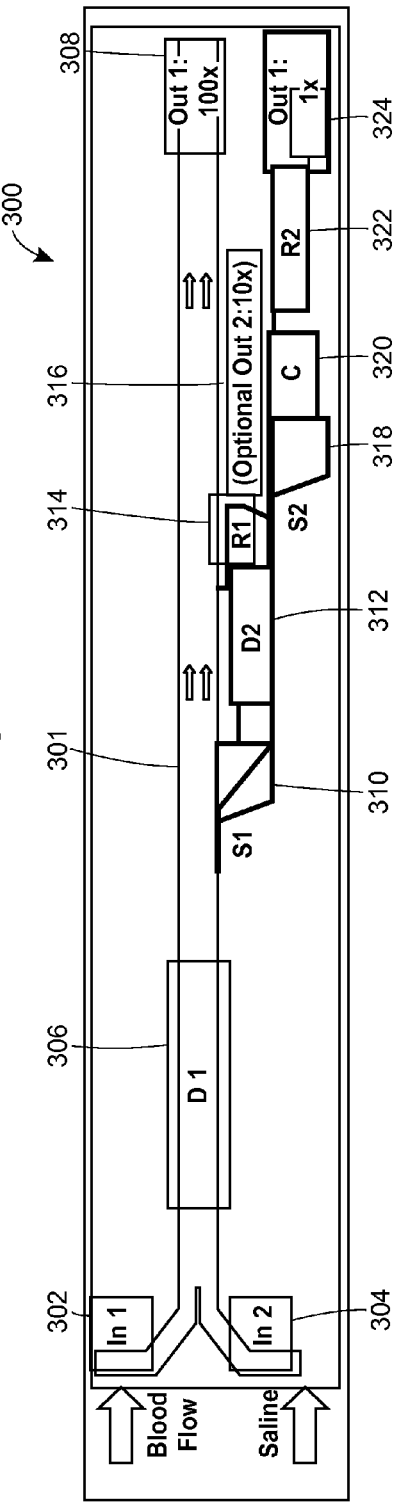
FIG. 2
FIG. 3

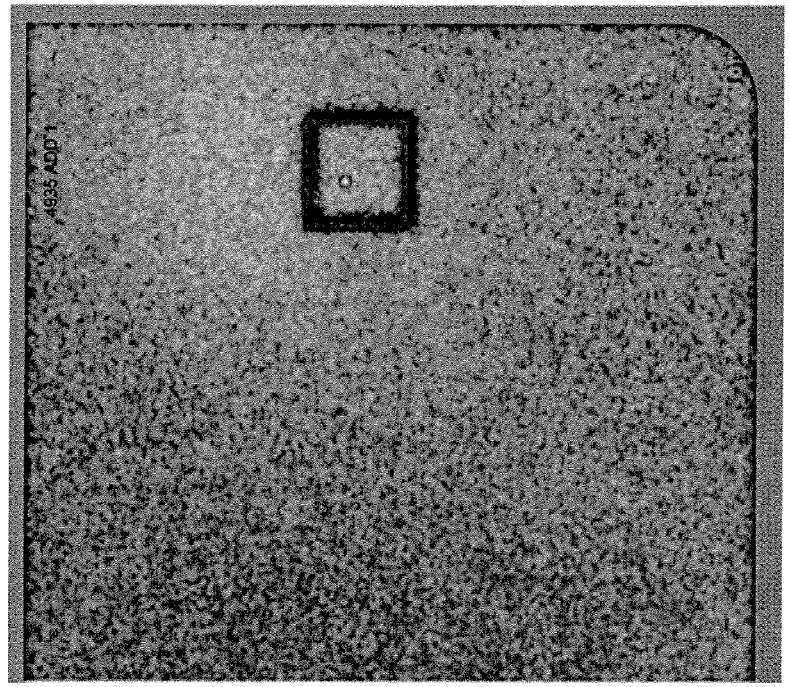
FIG. 7C
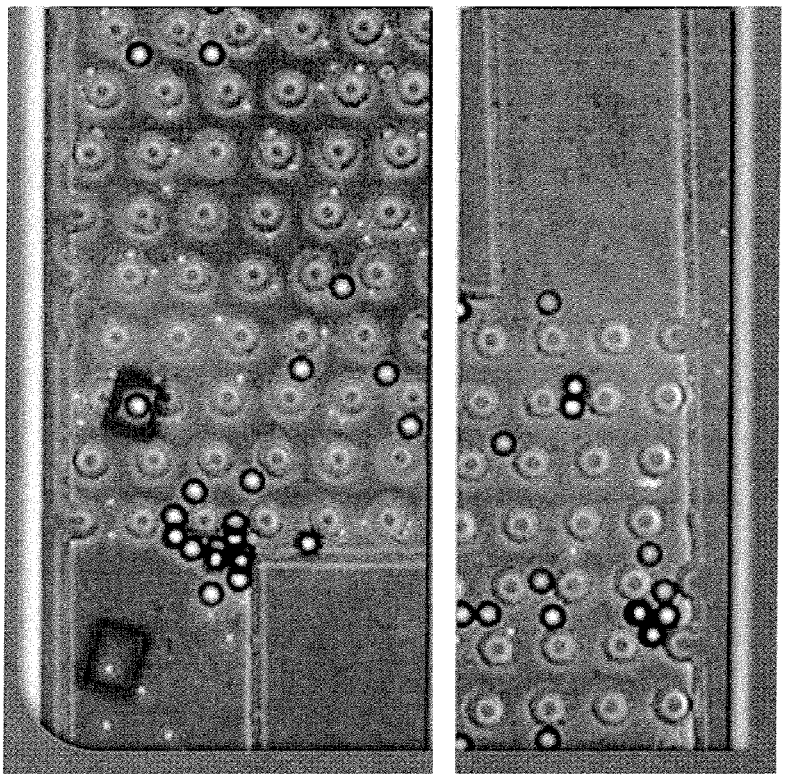
FIG. 7A
FIG. 7B

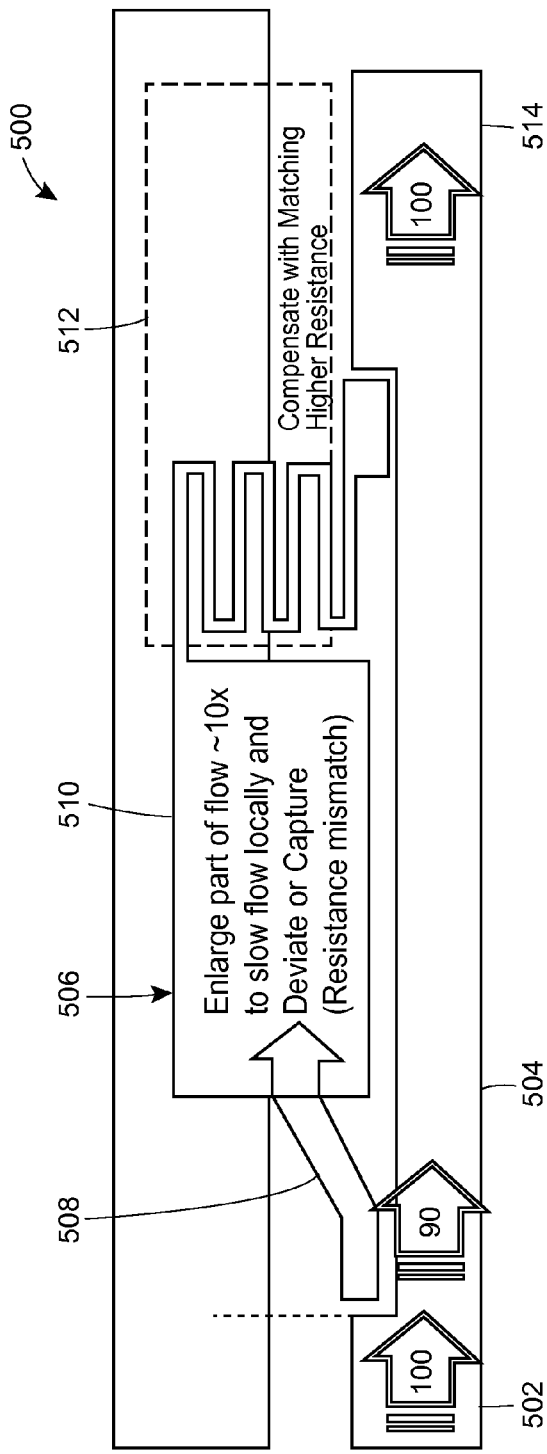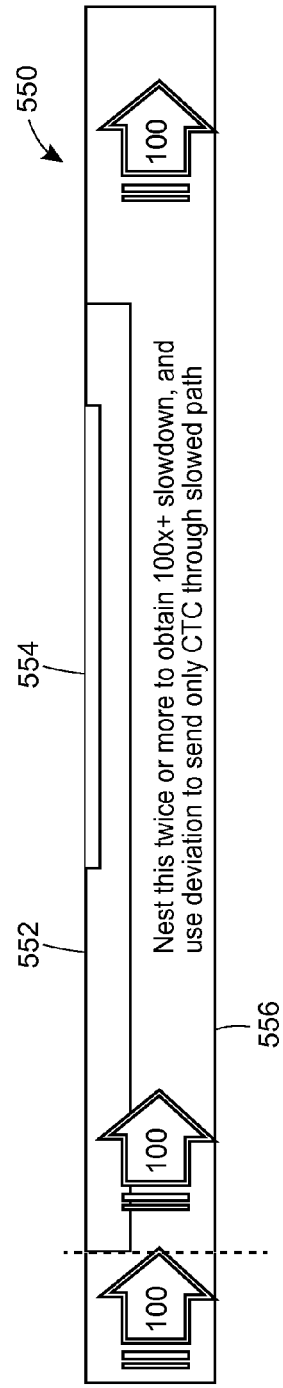
FIG. 13A
FIG. 13B

CIRCULATING TUMOR CELL CAPTURING TECHNIQUES AND DEVICES

CROSS-REFERENCE TO RELATED APPLICATIONS

This application claims priority to U.S. Provisional Application No. 61/593,092, entitled "Circulating Tumor Cell Capturing Techniques and Devices," filed Jan. 31, 2012, which is hereby incorporated herein in its entirety.

FIELD OF TECHNOLOGY

The present disclosure relates generally to recognizing, sorting, and isolating cells and, more particularly, to techniques for capturing circulating tumor cells from blood.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Circulating tumor cells (CTCs) are cells that sporadically release from a primary tumor and circulate in the bloodstream. Because CTCs travel in the blood stream, they may spawn growth of additional tumors in different tissues, creating a condition known as metastasis. CTCs, therefore, offer medical professionals a mechanism for identifying potential sources of tumor growth. Increasingly, CTCs are examined (in place of biopsies) during chemotherapy, radiation therapy, surgery, and other cancer treatments to assess treatment effectiveness and the likelihood of cancer spread.

There are three general techniques for CTC measurement. Size- and weight-based separation techniques generally require placing a blood sample in a test tube and isolating CTCs based on size, weight, or electric charge drift, also termed gradient centrifugation. Such techniques have various problems, stemming from the non-uniformity in size of CTCs and the inability to distinguish white blood cells from CTCs. Another technique uses microfilters, such as membrane filters, in an attempt to capture CTCs based on size differential. Yet another technique uses immunological methods to target and isolate CTCs. These latter techniques include magnetic separation techniques where magnetic beads are introduced into a cell mixture and bound with a CTC antigen, which is then examined. These latter techniques also include immunoaffinity techniques where a CTC is captured by a surface antigen bound to a substrate or post. In theory, the ability to count CTCs and test them using any of these techniques could help with diagnosis, prognosis, and determinations of preferred choices of treatment. In practice, however, the techniques are limited in effectiveness.

Many of the current CTC measurement techniques involve bulky and expensive setups. This is particularly true for immunological techniques, e.g., those based on expression of a putative tumor-associated biological marker or a tissue-type specific marker such as those of immuno-based or rtPCR-based strategies.

Moreover, all of the techniques are performed offline, in a laboratory, which slows measurement and often requires numerous CTC samples to achieve accurate measurement. Indeed, measurement times are a major limitation for CTC techniques. For one, CTCs move within the blood stream at such fast flow rates that capture is a difficult and inefficient process. CTC measurements, therefore, are performed externally to the body, for example, by using samples of blood collected over a period of time. But CTCs shed randomly and can die in the body, meaning that merely trying to draw blood and measure for CTC presence at any given point in time can result in false negatives, with existing systems. Additionally, the number of CTCs produced can depend on cancer type, which means that the number of samples needed to measure for CTC presence can vary, depending on the cancer type in the primary tumor.

Even with the most common CTC measurement technique, immunological techniques based on marker expression, current techniques are highly dependent upon the sensitivity and specificity of the reagents used for CTC marking (antibodies, rtPCR primers, invasive phenotype in collegen, etc.). The result is that techniques can miss upwards of 50%-100% of the CTCs in the blood, as that many CTCs may not express those markers, that includes cancer cells that might be the most biologically significant, such as cancer stem cells. The resulting biologic noise associated with low sensitivity and selectivity is thus a limiting factor, as is the low number of CTCs at any given time. Take, for example, 10 mL of blood, which may have billions of blood cells, billion of platets, millions of white blood cells, and anywhere from zero to a couple to a few hundred CTCs. To identify from among the main cancer types (breast, lung, colon, ovary, and prostate cancer, i.e., the "big five"), markers are chosen based on epithelial cell function. Epithelial cells produce keratin and Epithelial cell adhesion molecule (EpCAM), which can be expressed by markers. But not all cells that make cancer come from the epithelial cells form EpCAM. Some cancer cells will not make EpCAM, while other cancer cells may down-regulate EpCAM production until the cells have moved to a different location where they become active again. The result is that these biological-marker techniques may only see 50% of the CTCs.

SUMMARY

The present disclosure describes techniques and devices that address the limitations of conventional systems in a number of ways. The present techniques allow for faster measurement of CTC presence, without using a filter or, in some examples, without immunological separation. The techniques that may be implemented ex vivo, indwelling, or in vivo and used to isolate cancer cells based on size and flow dynamics. CTCs may be collected to identify epithelial versus mesenchymal cells, cancer versus normal epithelial cells, expression predictive markers, the presence or absence of a cell mutation, the presence or absence of a protein, the level of protein expression, cancer stem cell markers, and for whole genome next generation sequencing. For cancer related devices, any cancer cell, regardless of tumor source, may be identified, thereby allowing for devices that determine the total number of captured CTCs as an indication of a positive response to treatment (e.g., when the total number of CTCs declines over time) or a negative response to treatment (e.g., when the total numbers flatten or increase), for example. When captured in an external (ex vivo) device, CTCs may be collected and identified at any controllable flow rate or buffer condition, from real time to collection over hours. For indwelling and in vivo testing, CTC capture and measurement may occur by coupling a device directly to a patient, providing both intake and return paths for blood. In any event, with the present techniques, measurement time need no longer be a limiting factor.

The techniques are adaptable and can be implemented in a stand-alone measurement module or integrated into other systems. Further, the techniques may be implemented in real time and on a continuous basis, where they are able to sample blood over many hours, without removal. Further still, the techniques may be implemented, in some examples, in small and fast operating devices that can be implanted in a patient and used to continually measure for CTC presence over an extended window of time. In some examples, the devices may be implemented as chips that collect blood and separate CTC cells from blood cells based on differential flow dynamics and size, through a multi-stage assembly. These chips may be designed on the micron scale, for example, for better scaling in single stage or integrated systems. In some examples, devices have two flow channels, one for a blood specimen and at least one other for fluid containing the CTC. In some examples, blood is isolated exclusively in the blood flow channel to prevent the presence of any red or white blood cells in the one or more CTC flow channels.

In various examples described herein, the CTC flow channels are formed of different stages in a serial configuration, which are collectively positioned in parallel to the blood flow channel, where in some examples this parallel configuration includes coupling points between flow paths. The techniques are thus able to use serial stages, e.g., that each rely on both cell deflection and serially decreased flow rate in each successive stage, to separate out CTCs.

The CTCs may be collected in a capture chamber, for use in biological study, characterization, in vitro sensitivity to therapy assay testing, super-resolution microscopy, continual monitoring of patients, or other analysis techniques. Within the capture stage, the CTCs may be grown, in culture, as desired.

In some examples, devices have a single inlet and outlet, flowing only blood and concentrating and capturing CTCs while allowing surrounding blood cells to flow everywhere within the device. Although, in other examples, devices may use two inlets and two outlets, generating a protective laminar flow of saline solution that prevents blood cells from entering the capture area where CTCs are deflected and concentrated to and that may provide upwards of 100% purification from blood cells.

In accordance with an embodiment, a device for separating candidate cells from a carrier fluid, the device includes: a separation channel to receive the carrier fluid having a first flow rate and to provide for an isolation fluid, wherein the separation channel is configured to deflect the candidate cells from the carrier fluid into the isolation fluid; and a capture stage coupled to the separation channel through a coupling stage, wherein the coupling stage is configured to collect the isolation fluid and reduce the flow rate of the isolation fluid and deflected candidate cells, and wherein the capture stage is configured to capture the deflected candidate cells over a sampling period.

In accordance with another embodiment, a wearable circulating tumor cell capture device, the device includes: a mounting for releasable attaching the device to an exterior of a patient; an extraction lumen coupled to a vessel of the patient to continuously receive blood, at a normal blood flow rate, over a sampling period; a separation channel coupled to receive the blood at the normal blood flow rate and configured to deflect circulating tumor cells from the blood into an isolation channel and configured to maintain blood at the normal blood flow rate in main flow channel, where the separation channel blocks white blood cells and red blood cells from deflection into the isolation channel; a capture stage coupled to the isolation channel and configured to collect the deflected candidate cells over the sampling period; and an insertion lumen coupled to the vessel to re-introduce blood into the vessel at an acceptable blood flow rate.

In accordance with yet another embodiment, a method for capturing circulating tumor cells from blood, the method includes: maintaining blood flow at a normal blood flow rate and in a laminarized profile; deviating the circulating tumor cells from blood, while the blood is flowing at the normal blood flow rate; slowing the deviated circulating tumor cells; and capturing the slowed deviated circulating tumor cells.

In accordance with yet another embodiment, a device for characterizing cells within blood, the device includes: a plurality of deviation stages each functionalized to deviate cells within the blood based on a different morphological, mechanical, physical or biological characteristic; and a plurality of capture stages, each coupled to a different combination of the plurality of deviation stages, such that each capture stage corresponds to a different combination of physical and/or biological characteristics.

In accordance with yet another embodiment, a candidate cell analysis device includes: a deviation stage configured to deflect candidate cells from blood while the blood is flowing at normal patient blood flow rate, where the candidate cells are deflected into a blood-free solution; a slow down stage to slow the flow rate of the blood free solution having the candidate cells; and a capture stage coupled to the slow down stage to collect at least some of the candidate cells against further flow; and a cell detection readout device positioned to detect whether the candidate cells have been captured in the capture stage.

In accordance with yet another embodiment, a circulating tumor cell capture device, the device includes: a separation channel to receive blood from a vessel of a patient at the normal blood flow rate and configured to deflect circulating tumor cells from the blood into an isolation channel and configured to maintain blood at the normal blood flow rate in main flow channel, where the separation channel blocks white blood cells and red blood cells from deflection into the isolation channel; and a capture stage coupled to the isolation channel and configured to collect the deflected candidate cells over the sampling period.

There are numerous uses of the present techniques and in particular for integrating the capture stages herein into existing and/or standalone applications. For example, the techniques may be implemented in a device for CTC enumeration (counting cells) in a patient's blood, which can offer greater sensitivity and specificity over conventional CTC counting devices based on other counting techniques. CTC count is known to be prognostic in patients with metastatic breast, colorectal, and prostate cancer, for example. The techniques can be used to capture cells and stain them within the capture stage for various markers of biological and clinical importance: such as Estrogen receptor, HER2, and others described herein and elsewhere known. The capture stages are much more amenable to in situ staining compared to conventional systems. The techniques may be used to capture cells and then remove them capture stage for special studies, including single cell or multiple cell multi-gene expression or genomics, growth of CTC in culture or placed into a mouse for growth, and others.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A and 1B illustrate example flow diagrams of circulating tumor cell (CTC) capturing techniques according to some examples herein.

FIG. 2 is a block diagram of a CTC capture device in accordance with an example.

FIG. 3 illustrates a fabricated version of the CTC capture device of FIG. 2.

FIG. 5B is an image of the outlet end of a capture stage of FIG. 3 at a time, T=0, while

FIG. 6A is an image of an inlet portion of a capture stage; FIG. 6B is an image of an outlet portion of that capture stage; FIG. 6C is an image of a portion of the expanded region of the capture stage; and FIG. 6D is an image of a main channel of a CTC capture device, showing that no stained CTCs appear that main flow channel.

FIGS. 7A-C provides images of different portions of a CTC capture device, where FIG. 7A is an image of an inlet of a capture stage; FIG. 7B is an image of an outlet of the capture stage; and FIG. 7C is an image of an expanded central region of the capture stage.

FIG. 13A illustrates a CTC capture device in accordance with another example design implementation, having a nested stage.

FIG. 13B illustrates a CTC capture device in accordance with another example design implementation, having multiple nested stages.

DETAILED DESCRIPTION

Figure 4:
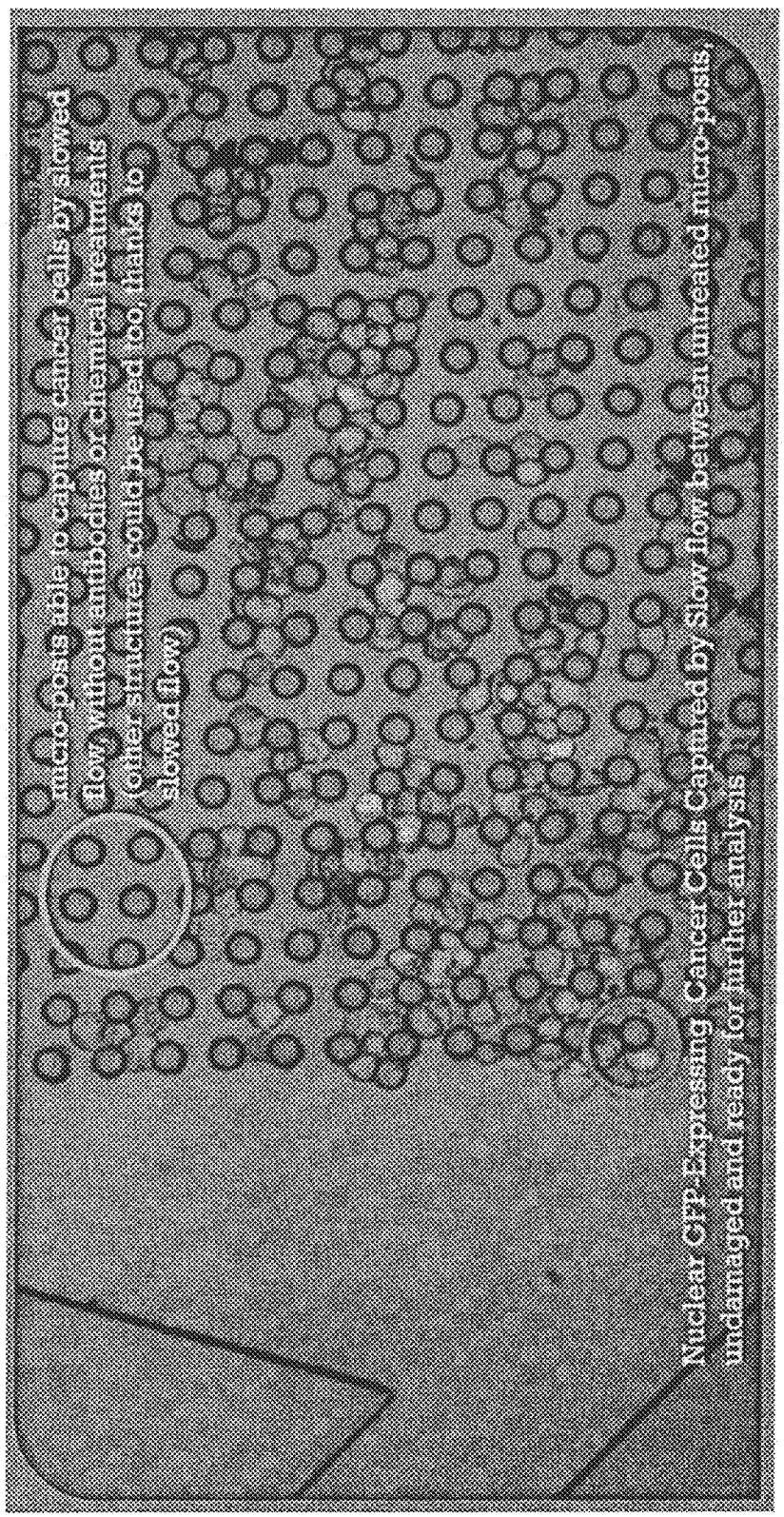
FIG. 4 is an image showing micro-posts and captured CTCs in a capture stage of the device in FIG. 3, in accordance with an example.

Generally, techniques described herein provide methods and systems for collecting candidate cells, such as CTCs using, for example, a multiple-stage device capable of handling high fluid flow rates, including flow rates at normal blood flow levels. In some examples, the techniques rely upon separation of CTCs from blood and slowdown of CTC flow, allowing CTC capture to occur. The techniques may deploy serial stages each rely on both cell deflection and serially decreasing flow rate in each successive stage to capture CTCs. The use of multiple stages provides modularity to control the amount of slowdown of the CTC flow rate and the channel sizes of the device used to separate, isolate, and capture CTCs. More generally, the present techniques allow control of numerous aspects of CTC measurement, including rate of fluid flow, the percentage of CTC collected (i.e., the sensitivity or recovery percentage or efficiency), the amount of CTC collected, the size of the CTCs collected, and the purity of the collected CTC sample (i.e., selectivity). Indeed, the present techniques show unexpectedly strong results in capturing CTCs with high sensitivity and selectivity.

In some example embodiments, the devices are built upon two principles: (i) deflecting CTCs out of the blood stream and (ii) using a laminar-flow barrier to ensure CTCs are completely deflected from all other blood cells and serum (i.e., selectivity). The devices use differential flow speeds to help concentrate and localize CTCs from a large volume to a small value, from which the CTCs may be counted, measured, extracted, or even grown in culture. The purification of CTCs from blood eliminates the need for performing a washing step, because blood cells like white blood cells (leukocytes, etc.) do not enter the CTC flow area, as has been confirmed by measurement.

The techniques may allow for real-time CTC capture during normal blood flow, without stopping or substantially abating normal blood flow. In fact, blood may be withdrawn from the body for CTC extraction and re-introduced into the body without clotting or blockage, e.g., by maintaining that blood flow at normal, acceptable levels. Such implementations may be achieved whether using external devices or indwelling devices (e.g., including in vivo devices).

By using a multi-stage configuration, the devices may be designed to separate CTCs from blood cells using a flow channel separation process that occurs at normal or other blood flow rates. Blood may be maintained for flow in a blood flow channel, while CTCs are made to flow in a separate CTC flow channel. As the CTCs are separated from the blood, the CTCs are directed to the CTC flow channel comprising one or more additional stages (e.g., capture stages) in a serial configuration.

While the separation process may occur at a normal blood flow rate, the stages in the CTC flow channel may operate at a slower rate. For example, the CTC flow channel may be configured to capture CTCs flowing at 1/10, 1/100, or slower than the rate of the blood flowing in the blood flow channel. The exact amount of slowdown may be determined by the configuration and type of stages making up the CTC flow channel. By having the blood flow channel and the CTC flow channel in parallel, whether in a coupled or decoupled manner, the flow of CTCs may occur at slower flow rates while the originating blood may flow at normal blood flow rates. The blood flow channel may be coupled to the CTC flow channel to control resistance between the channels. Flow rates on the order of 1 ml/min to 10 ml/min and greater may be achieved through a CTC device.

In various embodiments, CTC separation is highly selective, meaning that no or substantially no other blood cells are separated with CTC separation. It is particularly helpful to separate CTCs from white blood cells, to prevent contamination of CTC measurement, because white blood cells may outgrow CTC in cell culture and confuse analysis testing. While in some examples, such selectivity is controlled by the initial separation stage, in other examples, separation and selectivity (i.e., the isolation of only CTCs) may be achieved using different stages.

Furthermore, CTC capture and measurement times are much lower than with conventional (gravity separation, filter, and immunological) techniques, in part, due to the ability to use higher flow rate. Instead of requiring many hours or days to capture CTCs, separation, capture and measurement may be achieved, in minutes, in some examples. Furthermore, where desired resulting devices may be used "on patient" for long periods of time, from minutes, to hours, to days, without removal. In this way, a single device may be used to measure CTCs when they are shed. By allowing for devices used over longer periods of time, periodic measurements may be made for the presence of CTCs, thereby allowing clinicians to eliminate false negative results from random shedding and CTC de-expression from apoptosis.

The present techniques may also be implemented in a label-free (marker-free) application, by substituting a size-based deflection stage with angled antibody-strip deflection stages in a cascading multi-stage device, as discussed in examples below. As a result, CTCs may be deviated into different capture stages based on markers they express as the CTCs travel over patterned deflection strips, i.e., a ligand-based capture. In this way, we can know which CTCs and how many of the total CTCs have a specific property or expressed by a specific antigen without binding to an antibody or reagent.

While the present techniques are described in reference to CTC measurement, more generally the present techniques may be used to separate, purify, and magnify any candidate cells, including epithelial cells, endothelial cells, neurons, hepatocytes, nephrons, glial cells, muscle cells, skin cells, adipcytes, fibroblasts, chondrocytes, osteocytes, and osteoblasts. The candidate cells may include rare or abnormal cells present in a biological fluid or fluid specimen, including cells indicating an abnormal condition, such as infectious disease, chronic disease, injury, or pregnancy. Candidate cells may include cells that are not normally present in a biological fluid or fluid specimen and cells that may be normally present but in low concentrations. Furthermore, the techniques may be used to separate cells from other cells, without cause to further separate those cells from blood.

FIG. 1A illustrates an example multi-stage CTC collection device 100, in which an incoming blood flow is drawn from a patient and combined with a water and/or saline flow at a combiner/splitter 102. The combiner/splitter 102 leads to a blood flow channel 104 that contains blood cells and only a fraction of residual CTCs and a CTC flow channel 106 that contains only captured CTCs and water or saline solution. It is noted that the channels 104 and 106, as well as the other channels described herein may be microfluidic channels, where "micro" as used herein refers to a structure having at least one dimension below 1 mm. The blood flow channel 104 continues into a blood capture stage 108, which in some examples (e.g., indwelling devices) function as a re-insertion stage where the blood is re-introduced into the patient. The CTC flow channel 106 feeds a multi-stage configuration formed of stages 110-114, in the illustrated example. The stages 110 and 112 are slow down stages that reduce the flow rate of the CTC fluid received from channel 106. The final stage 114 is a collection stage where the CTCs are accumulated. The particular implementations will vary.

FIG. 1B illustrates a similar example embodiment 100' to that of FIG. 1A, but with only one slow down stage 110' and the capture stage 114'.

In the illustrated example of FIG. 1A three stages are shown; but it will be understood that any number of stages, greater or smaller may be used, as desired. Furthermore, the stages 110-114 may operate based on micro-fluid dynamics to isolate CTCs, without the need to detect CTC markers. However, as discussed in some detailed embodiments below, in some examples the techniques may be used based on antibodies and specific antibody deflection.

FIG. 2 illustrates an external example CTC capture device 200 in accordance with an example embodiment and in a block configuration. Blood flow enters at a first position having a first inlet (In 1) 202 and a saline solution enters at a second position coinciding with a second inlet (In 2) 204. It is noted that while a saline solution is shown, the solution may be water or some other fluid suitable for maintaining laminar flow. The inlet stage (both In 1 and In 2) is coupled to a first deviation stage (D1) 206, where separation of the combined saline solution and CTC from the blood blow occurs, resulting in an outlet stage (Out 1) 208 within which blood continues to flow, at least initially, at normal blood flow rate (indicated at 100× in relation to the flow rates of the CTC flow channel discussed below).

Defining a CTC flow channel, the deviation stage 206 is also coupled to a first slow down stage 210 that slows down the combined saline and CTC flow from the flow rate of the blood flow. The slow down stage 210, for example, slows down the flow rate by a factor of 10, in the illustrated example. The particular amount of slowdown may be determined based on channel geometry and specifically the ratio of channel widths in the forking channels at the exit of the deviation stage 206 and the ratio of downstream flow resistance in each forking path.

Constraints like the smallest size channel that will still allow cells to flow through provide limits to these slow-down factors and favor a multi-stage approach. Therefore, in the illustrated example, a second deviation module (D2) 212 is coupled to receive the slowed CTC flow from stage 210 and separate the CTC flow into an output channel and an isolated CTC channel. A high-resistance stage (R1) 214 and an outlet stage (Out 2) 216 are coupled to the output channel of the deviation module 212. The module 212 therefore provides a mechanism for further slowing down CTC flow. In the illustrated example, the outlet stage 216 provides purified solution at a flow rate of 10×, meaning 10× times the flow rate over the isolated CTC channel which is coupled to a second slow down module (S2) 218.

The isolated CTC channel begins with the slow-down module 218, which is a 10× slow down module, and feeds a capture area, or CTC accumulator, (C) module 220. The module 220 collects the CTC over the measurement time of the device 200. Capture is increased by a high resistance stage (R2) 222 positioned at the output of the module 220 between it and an outlet (Out 3) stage 224. While CTCs build up in the capture stage 220, the water or saline solution may continue to flow through the resistance stage 222 into the outlet stage 224, which occurs at a much reduced flow speed a value indicated as 1×, in comparison to the outlet 216, which has a flow 10× greater, and in comparison to the outlet 208, which has a flow 100× greater.

FIG. 3 illustrates an example microchip 300 (e.g., a lab-on-a-chip device) implementation of the device 200, where the various stages are shown (with like reference numbers in the 300 series instead of the 200 series). The device 300 was formed through a soft-lithography and PDMS molding and curing process, in which a polymer mold was used to form the shapes of the stages; and this mold was treated with tri-fluoro-silane to make the Polydimethylsiloxane (PDMS) detach from it. For mounting, plasma oxygen was used to bond the resulting structures to glass. The master molds may be fabricated in different ways, including Deep Reactive Ion Etching of silicon wafers and spincoating, baking, exposing and developing a layer of SU8 photoresist on silicon or glass. While the device 300 was formed using the described techniques, more generally, any number of fabrication techniques may be used to form the stages having micro sized features and other features, as discussed herein.

As shown in FIG. 3, in some examples, the outlet stage 316 (corresponding to stage 216) is optional.

Empirical testing was performed on the implementation shown in FIG. 3, which included a manual flow rate up to 4 ML/min (for H=100 μm) (~1 ML/min for H=50 μm). The device 300 was shown to capture >90% of spiked CTCs from blood, and for each of three different types of CTCs tested. Flow speed of the blood flow channel 301 relative to the final capture stage 324 was approximately 100× to 1×, which was measured by video of particle movement and the relative total volume moved through each channel.

It is noted that a range of flow rates may be used for a particular geometry device, but that beyond a point, if the flow rate is too fast then platelet activation may occur and blood clots may be formed. In such examples, a slower flow rate may be used or an anticoagulant, such as a blood thinner like aspirin, may be introduced into the device.

Further operation of the different stages in FIGS. 2 and 3 is now described with respect to some example implementations. Referring to both FIGS. 2 and 3, stages In1 and In2 may laminarize flow of the respective incoming flow streams, where laminarization allows for better separation in the deviation stage D1, without the need for 'washing' or purification. Stages D1 and D2 operate as deviation modules that are implemented by size separation, e.g., using designed micro-post geometries and orientations to deflect CTCs. In other examples, deviation may be achieved using deflecting agents, such as through antibody-rolling deflection, or other methods able to detect cells.

In the illustrated example, the deviation stages concentrate the CTCs in a portion of a flow, in particular in a lower portion of the laminarized flow as defined by the flow dynamics at the outlet of the deviation stage. When using micro-posts, the pattern deflects CTCs to one side of the channel while the red and white blood cells remain un-deflected, thereby separating the CTCs by size. The particular pattern may vary and different pattern sizes may be used to capture different CTCs. In an example, the deviation stage was patterned to deflect CTCs of 18 microns in size or higher.

In illustrated embodiments, the deflection pattern in the deviation stage is uniform across the entire stage. Yet, in other examples, the deflection pattern may vary depending on the desired flow conditions within the stage.

Stages S1 and S2 are slow down stages and may be adjusted in configuration and/or length to affect the amount of slow down. They expand the small flow channel to reduce speed.

Elements R1 and R2 provide resistance matching. These high-resistance connector modules are calculated in width and length to compensate and match resistances between the different paths and preserve specific flow ratios and flow speeds. Proper resistance matching allows one to use a smaller percentage of the flow instead of merely halving the flow through each deviation stage. While the R1 and R2 stages may be separate in some examples, in other examples, the resistor stage may be nested with other stages, as discussed further below.

Stage C provides low speed antibody-free capture on micro-posts. The capture area is designed to accept higher flow speeds, as necessary. In some examples, the stage D2 may serve as a capture stage, at least at lower speeds and depending on the deviation method used in the stage. More generally, the capture stage C and the deviation stages D1 and D2 may have the same or similar micro-post patterns, expect that the capture stage C is designed to accumulate CTCs, where that accumulation principally occurs in three regions: at the initial inlet of the C stage, in the middle expanse of the C stage, and/or at the outlet of the CTC stage.

Stages Out1, Out2, and Out3 represent three different outlets. Out1 is used to return the bulk of the fast-flowing material (e.g., blood) to the body where that material is mostly free from CTCs. Out2 may be kept separate or merged with Out1 as shown in FIG. 3. Out3 has ~1% of the flow of Out1 and generally contains only saline and possibly a small amount of the CTCs that were selected but not fully captured, in the capture stage. The small amount of CTCs that escape Out3 may still be counted by taking the resulting cells and putting them in a dish or microwell and looked under a microscope.

The CTCs trapped by the device can be counted, imaged, grown and/or analyzed easily with known techniques simply by placing the small approximately 2 mm capture area of the transparent device in focus under a microscope, or even in a slightly modified plate reader (for quick, cheap automatic counting) or in a cell culture incubator. Reagents for staining and washing for various measurement assays can be introduced through outlets like Out3 or introduced through any combination of existing inlets and outlets. In addition, cell detachment reagents like trypsin can be used to detach cells from the capture area of the chip so they are collected from Out3 into cell culture plate or other containers for further experimentation.

Once collected, the CTCs can be examined for subsequent biological study, characterization, in vitro sensitivity to therapy assay testing, immunofluorescence, super-resolution microscopy, or other analysis techniques. CTCs in a capture stage may be counted by any known techniques, including optical, visual inspection, automated counting, microscopy, and electrical detection. Any DNA analysis may be used, such as real time polymerase chain reaction. The CTCs, for example, may be collected from the capture stages for reverse transcription polymerase chain reaction (rtPCR), in which an RNA strand is first reverse transcribed into its DNA complement (complementary DNA, or cDNA) using an enzyme reverse transcriptase, and the resulting cDNA is amplified using traditional PCR or real-time PCR. In any event, through analysis, CTCs may be used to determine the tissue of origin, the stage or severity of disease, as well as the effectiveness of certain treatments. And as discussed, in some examples, the CTC techniques herein may be used in determining which treatments to apply based on cell type.

FIG. 4 illustrates an image showing micro-posts and captured CTCs in the capture stage 324 of the device 300. The image is a phase-contrast image showing features including posts and the other images are different fluorescent colors showing different markers and different parts of the cell (nuclei and cytoplasm). The micro-posts (the regular circles) are 30 microns or 0.03 mm in diameter. The CTCs have been pre-expressed with a nuclear green fluorescing protein (GFP) using a known procedure. The CTCs were then introduced into the blood. For this particular example, this pre-staining and spiking process was done for evaluation testing of the system, where only CTCs would fluorescence under examination. FIG. 4 shows that the CTCs are slowed down flow through the micro-posts.

In the illustrated example, the micro-posts are untreated, although in other examples they can be treated with antibodies as discussed below. The CTCs may pass through this stage, e.g., if the stage is implemented as a deviation stage, or collected and retained in the stage, in the case of a capture stage.

The micro-posts shown are generally cylindrical with circular cross-sections, although other shapes can be formed, including triangular, rectangular, octagonal, and polygonal shapes, or combinations thereof. Further the micro-posts are shown aligned in a generally arrayed configuration. Other array configurations may be used including a simple equidistant array, while in yet other configurations, a linear or partially linear structure may be used, such as a herringbone-shaped structure used to form one or more of the stages. The spacing and patterning of the micro-posts may be selected based on the expected mean diameter of the cancer cells under examination and based on desired specificity/selectivity characteristics. The spacing and patterning may be selected to promote various amounts of clustering of cancer cells within capture stages, as examples herein illustrate that CTCs may be captured at different locations within a capture stage and clustered to differing amounts. Further the spacing between micro-posts may be determined as discussed further below.

In some tests, it was measured that only about 5% of the CTCs went un-captured, meaning that complete separation of blood from CTCs was highly effective. This was measured for approximately 4 mins, across 1 ml of blood in which 350 spiked cells (Hela-GFP) were captured, with 1 ml PBS (phosphate buffered saline). In that example, the CTC was a Hela cell line, a type of Epithelial cervical cancer, made easier to detect and verify by addition of a nuclear GFP transfection. The measured recovery rate (i.e., efficiency or capture yield) was 92%.

Figure 5A:
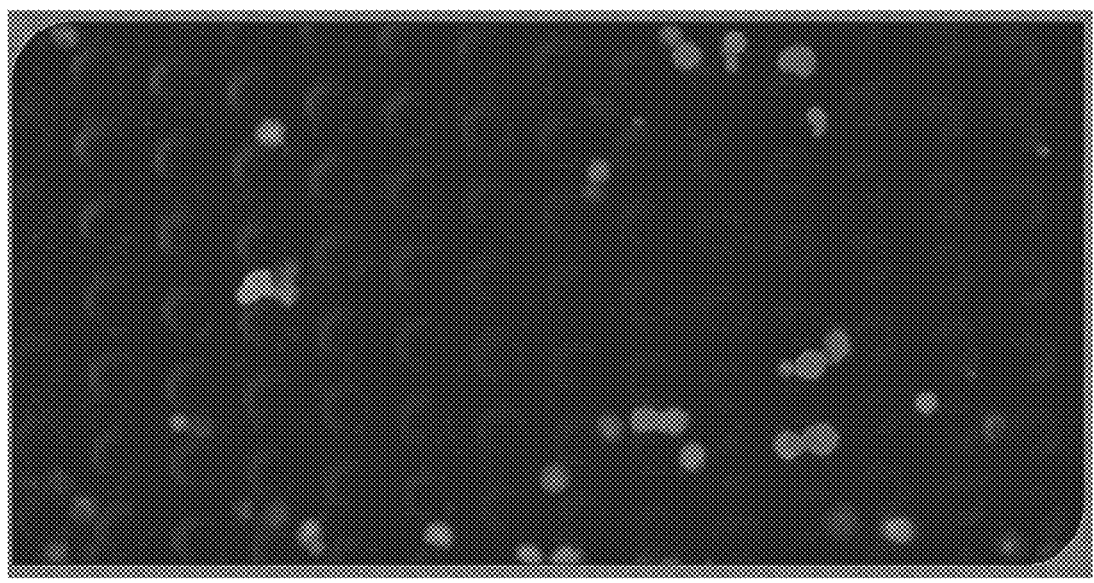
FIG. 5A is an image of a capture stage of the device in FIG. 3 capturing CTCs, in accordance with another example.

FIG. 5A is a similar illustration to that of FIG. 4 except that the image resulted from testing on a second type of CTC, specifically 150 cells of the MDA-231 type (mesenchymal breast cancer cell) stained with anti-cytokeratin. Green fluorescence indicated the presence of a CTC, as shown by lightened circles in the image. A control was used, specifically anti-CD45. The recovery rate of CTC was shown to be 90%+, in this example.

Figure 5C:
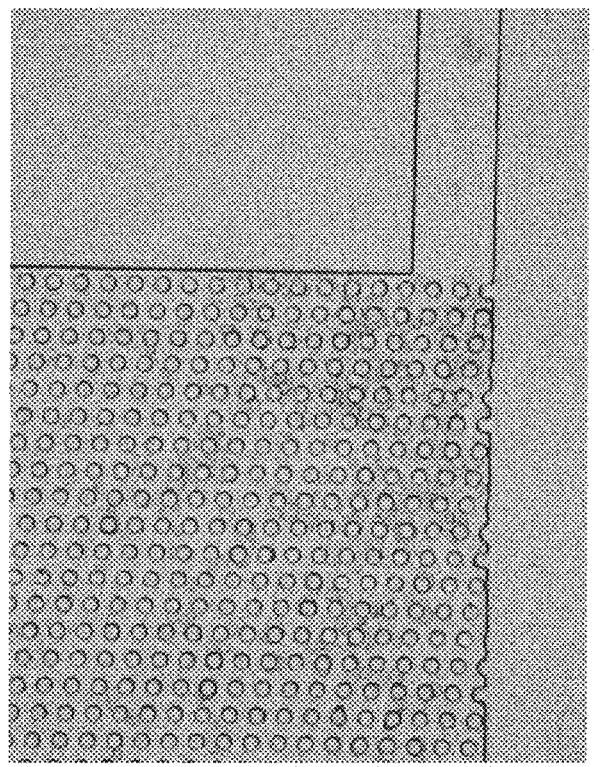
FIG. 5C is an image of the same at a time, T=18, in accordance with an example.
Figure 5B:
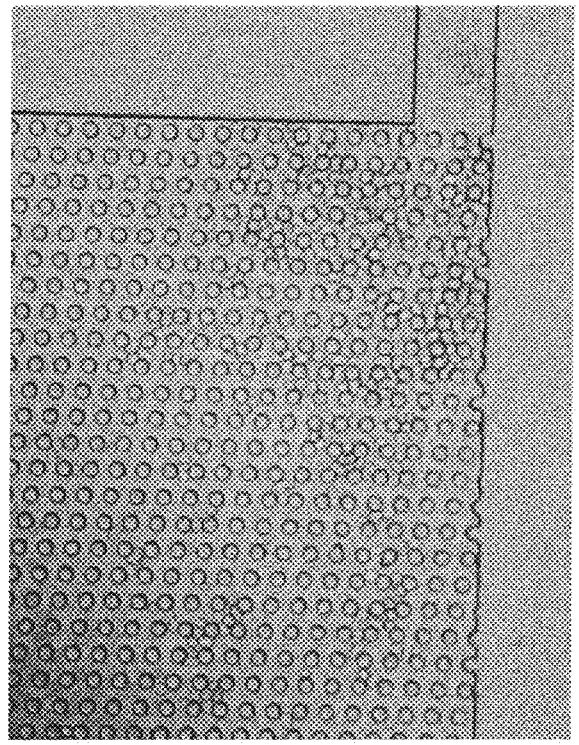

FIG. 5B is an image of the outlet end of the capture stage 234 at a time, T=0, while FIG. 5C is an image at a time, T=18 hours showing accumulation of CTCs and some spreading of CTCs from the outlet into a resistance stage, only partially shown.

Figure 6A:
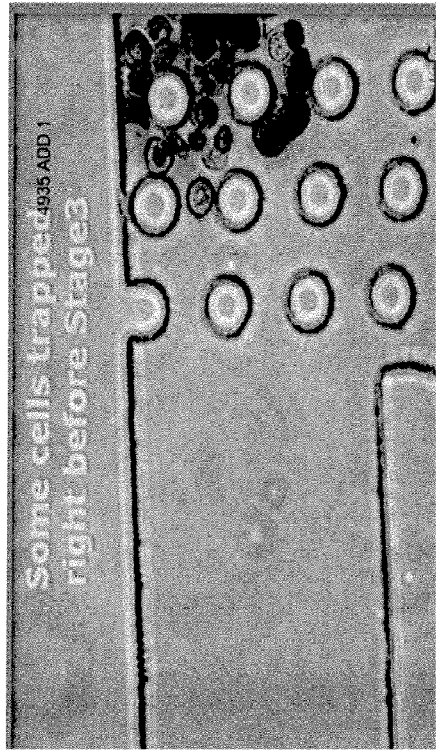
FIGS. 6A-6D provide images of different portions of a CTC capture device, where
Figure 6C:
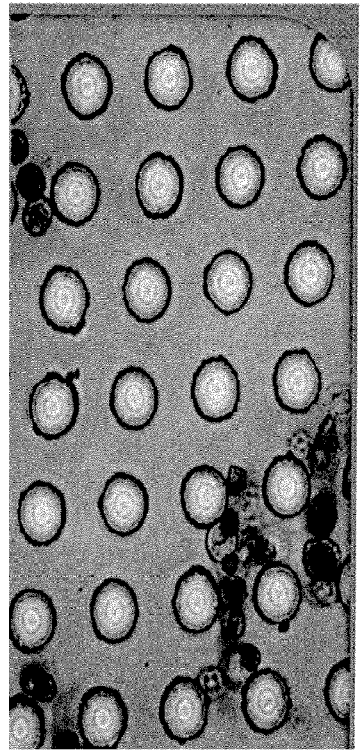
Figure 6B:
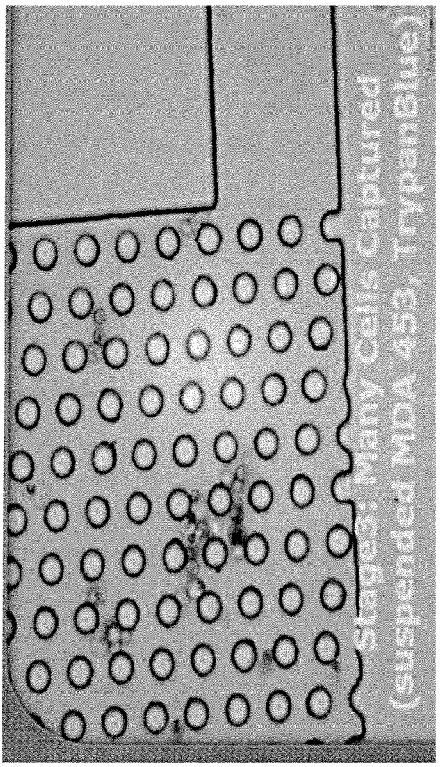
Figure 6D:
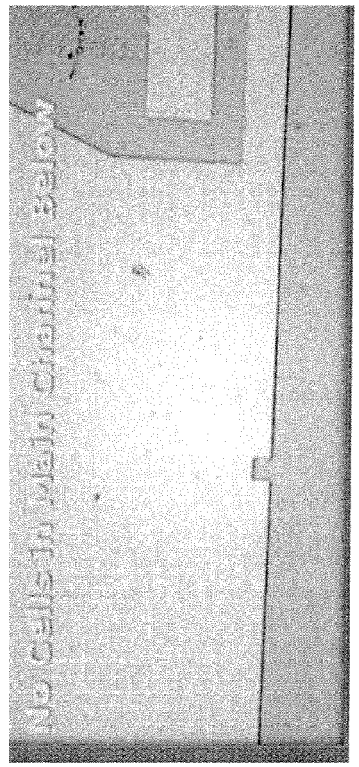

FIGS. 6A-D illustrates a similar image to that of FIG. 4 showing an image resulting from yet another example implementation for a third type of CTC, specifically for the MDA-453 type (suspended luminal breast cancer cell) fixed and stained with TrypanBlue. Recovery rate of 90%+ was shown. FIG. 6A illustrates an inlet portion of the capture stage 324; FIG. 6B illustrates an outlet portion of the capture stage 324; FIG. 6C illustrates a portion of the expanded region of the capture stage 324; and FIG. 6D illustrates the main channel, showing that no stained CTCs appear in main flow channel 301.

FIGS. 7A-C illustrates an example of a negative control, using blood and 20 micron beads, and illustrating an inlet of the capture stage 324 (FIG. 7A), an outlet of the capture stage 324 (FIG. 7B), and the expanded central region of the capture stage 324 (FIG. 7C). The recovery rate was 95%+ for recovery of larger perfectly spherical beads, while the system resulted in 0% false CTCs identified.

Figure 8A:
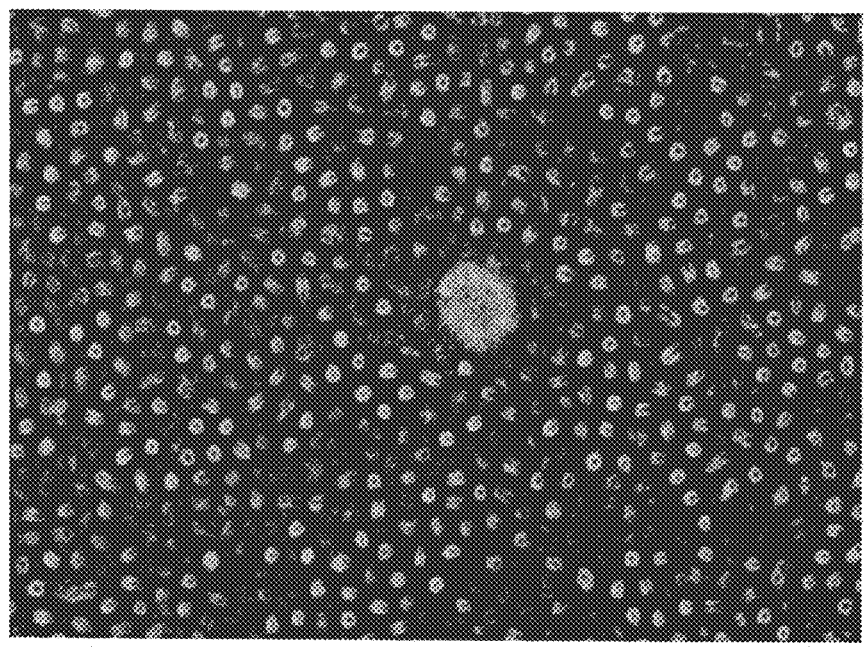
FIGS. 8A-8B are images of an example test using the CTC capture device of FIG. 3, in accordance with another example.
Figure 8C:
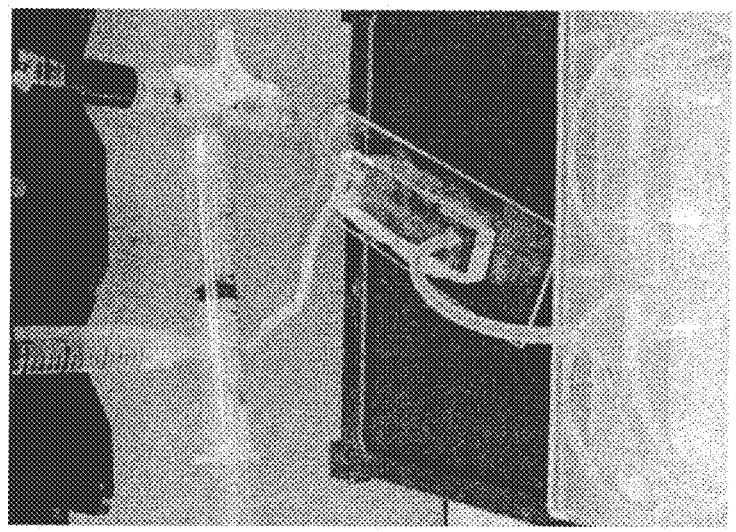
FIG. 8C is a photograph of an experimental setup for the CTC device of FIG. 3.
Figure 8B:
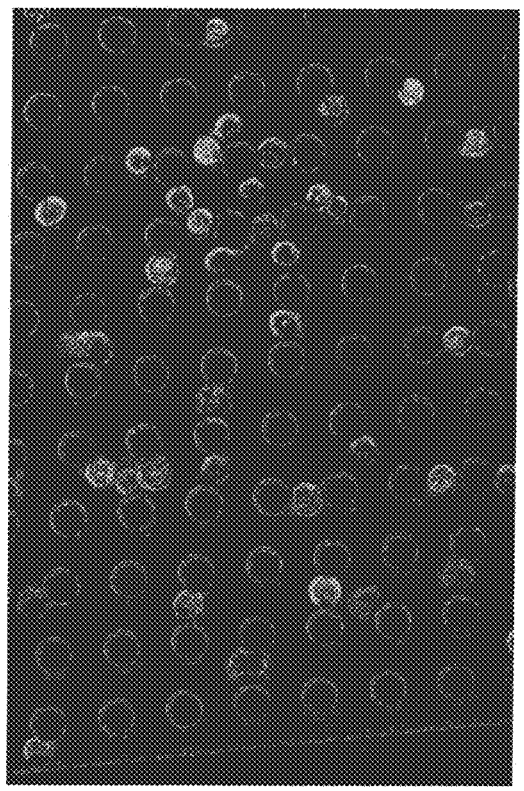

FIGS. 8A-8C illustrate another example test of the device 300. FIG. 8A illustrates a BT-474 cancer cell stained with fluorescent dyes (nucleus is blue and cytoplasm is green) and then mixed with millions of blood cells. FIG. 8B illustrates the same stained cancer cells completely purified, concentrated and captured from blood into the capture stage 324 of the device 300, showing that the capture stage 324 is free from any blood cells. FIG. 8C illustrates the experimental setup for the CTC device 300 in the process of separating cancer cells from fast-flowing blood.

Figure 9A:
FIGS. 9A-9G are images from an example test of the device of FIG. 3.
Figure 9C:
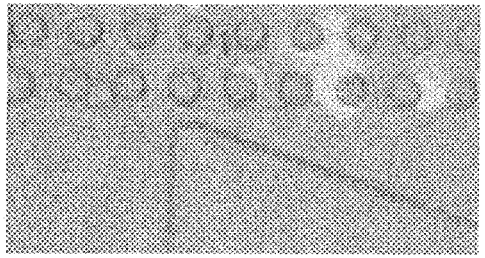
Figure 9B:
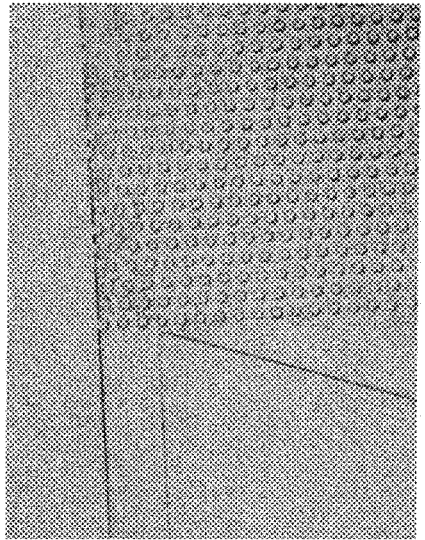
Figure 9D:
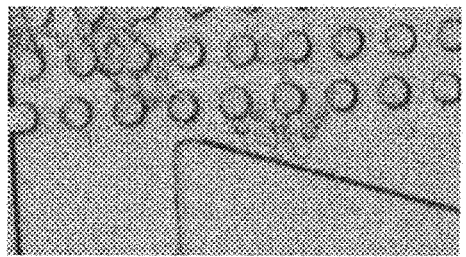
Figure 9E:
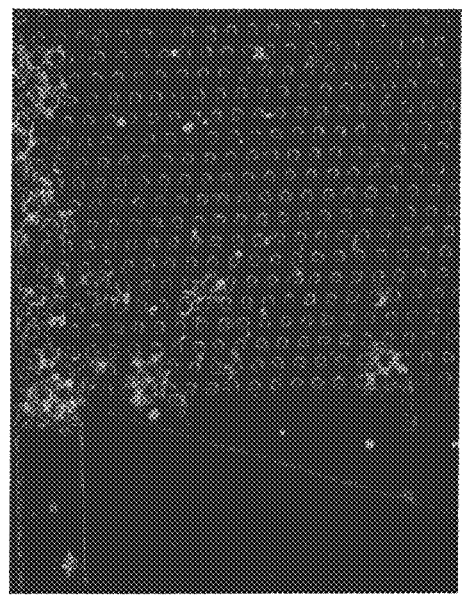
Figure 9F:
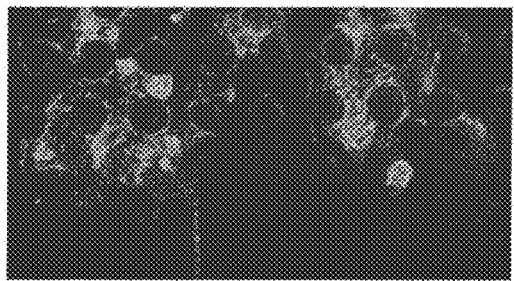
Figure 9G:
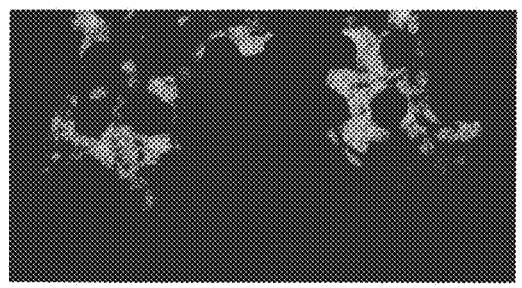

FIGS. 9A-9G are images from another example test of a CTC device. FIGS. 9A and 9B are microscopy (e.g., phase contrast images) of an inlet region of a capture stage show accumulation of cells, while FIGS. 9C and 9D are similar images showing fluorescence response confirming that the accumulated cells are stained CTCs. FIGS. 9E-9G are images of the capture stage showing cells captured alive and grown for two weeks inside the device (demonstrating capability for even long-term live biological response testing of CTCs), and stained after the second week with antibodies for ER (red) and HER2 (green) for cells that are mostly negative in HER2 (demonstrating the ability to detect important biological markers even within the device). Nuclei are shown with DAPI staining, blue in FIGS. 9E and 9F, and shown alone in grayscale in FIG. 9G for clarity.

Figures 10A, 10B, 10C:
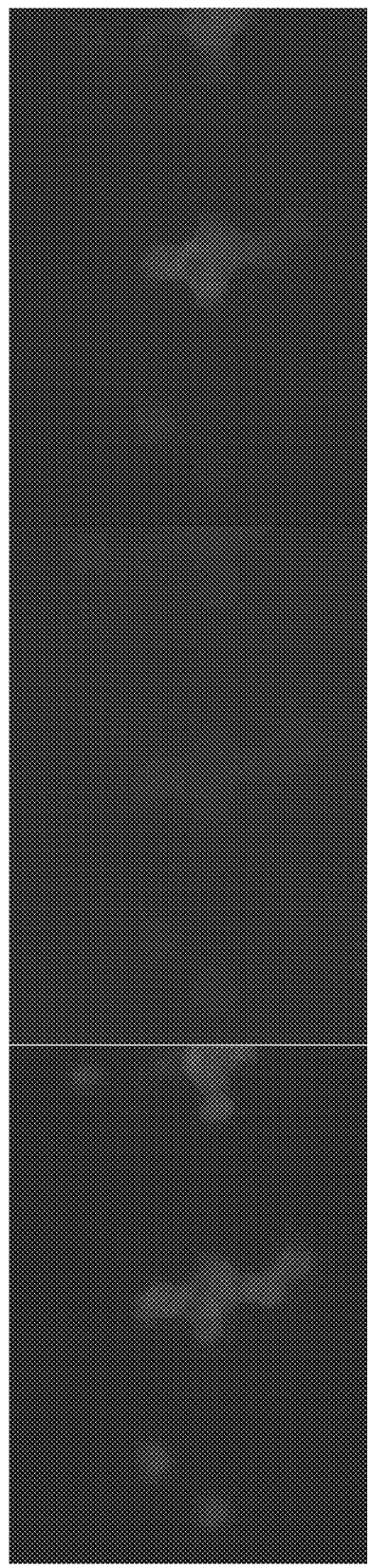
FIGS. 10A-10F are images from another example test of the device of FIG. 3.
Figures 10D, 10E, 10F:
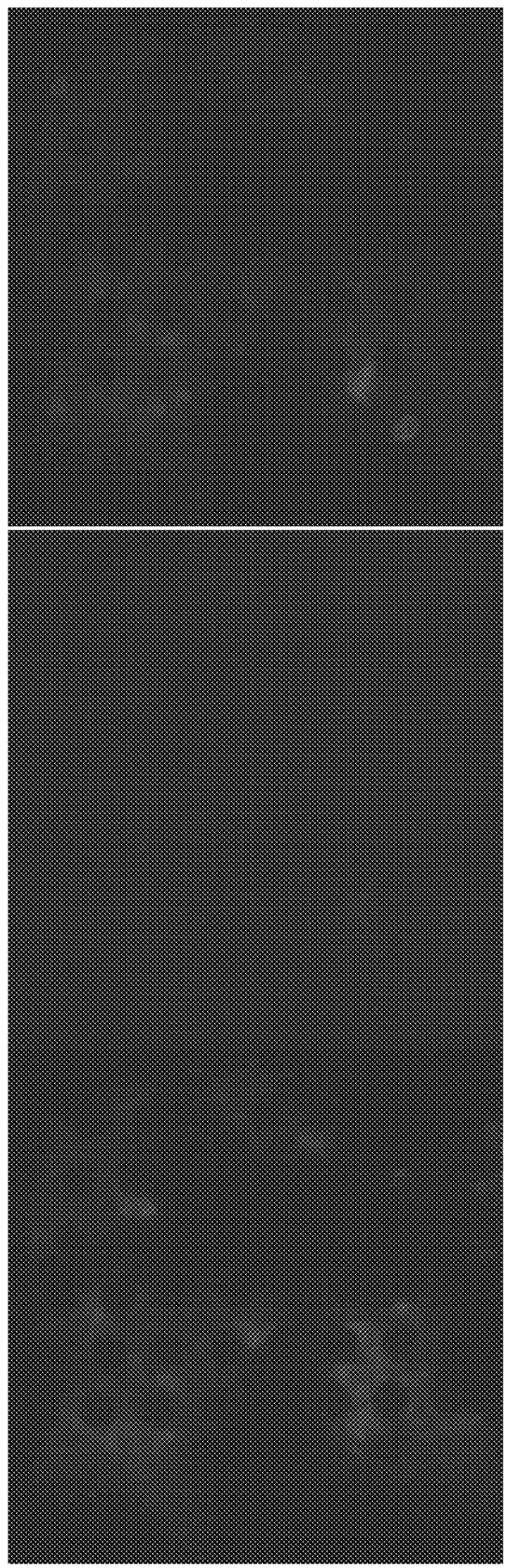

FIGS. 10A-10C are images from yet another example testing of the device 300, showing the cells stained immediately after capture: DAPI (FIG. 10A), HER2 (FIG. 10B), and ER (FIG. 10C) for a first region of a capture stage. FIGS. 10D-10F are similar images but over a different portion of the capture stage.

Figure 11:
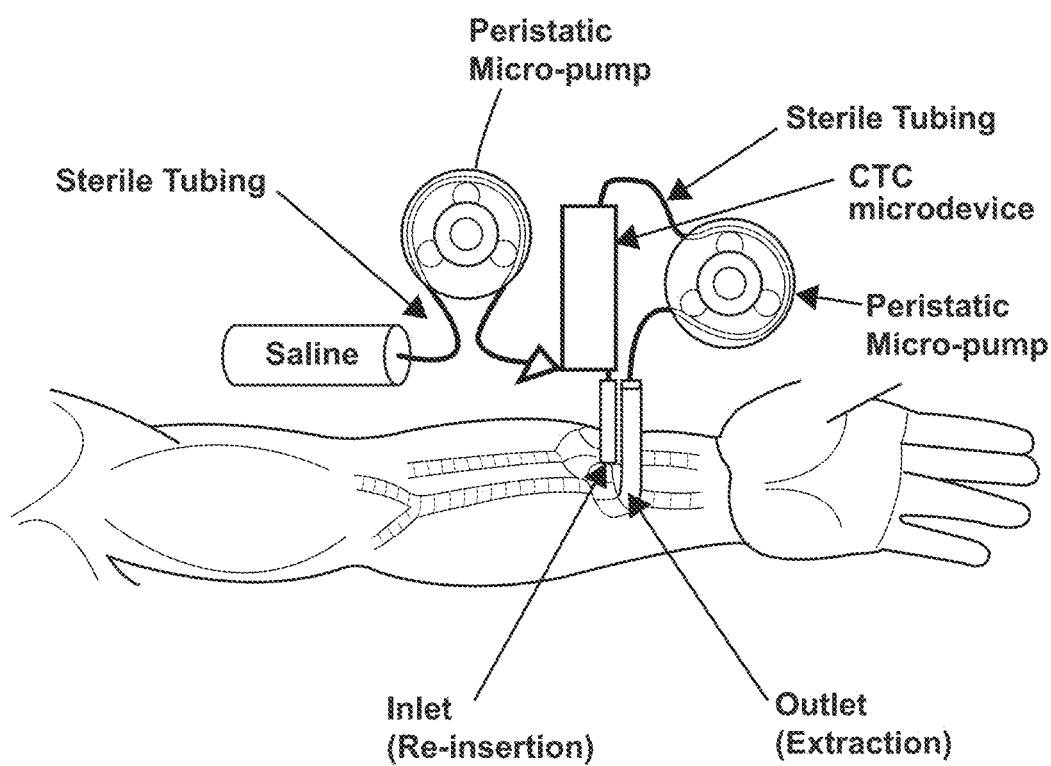
FIG. 11 illustrates real-time CTC capture device that re-introduces blood collected from a patient back into the patient, in accordance with an example.

The techniques, while discussed above in various example embodiments, may be modified for use in any number of ways. For example, devices can be mounted as an indwelling intravenous catheter device or a wearable point-of-care device (as shown in FIG. 11) operating as an extravenous device (similar to a mini/micro-dialysis machine) for prolonged monitoring of rare CTC-shedding events. FIG. 11 illustrates a connected real-time CTC capture device. In some implementations, the device may be connected to a patient's arm with two needles, one for blood drawing and the other for blood return, functioning somewhat like a micro-dialysis machine. A small check-valve micropump is used to aid flow through the device. A small amount of saline solution is added to circulation, for example using a separate tubing and micropump. A commercially available micropump from WELCO (Tokyo, Japan) may be used. Blood is able to exit and re-enter the body at normal blood flow rates, without clotting or blockage, while CTCs are collected away from the blood and can be accumulated over time.

Figure 12:
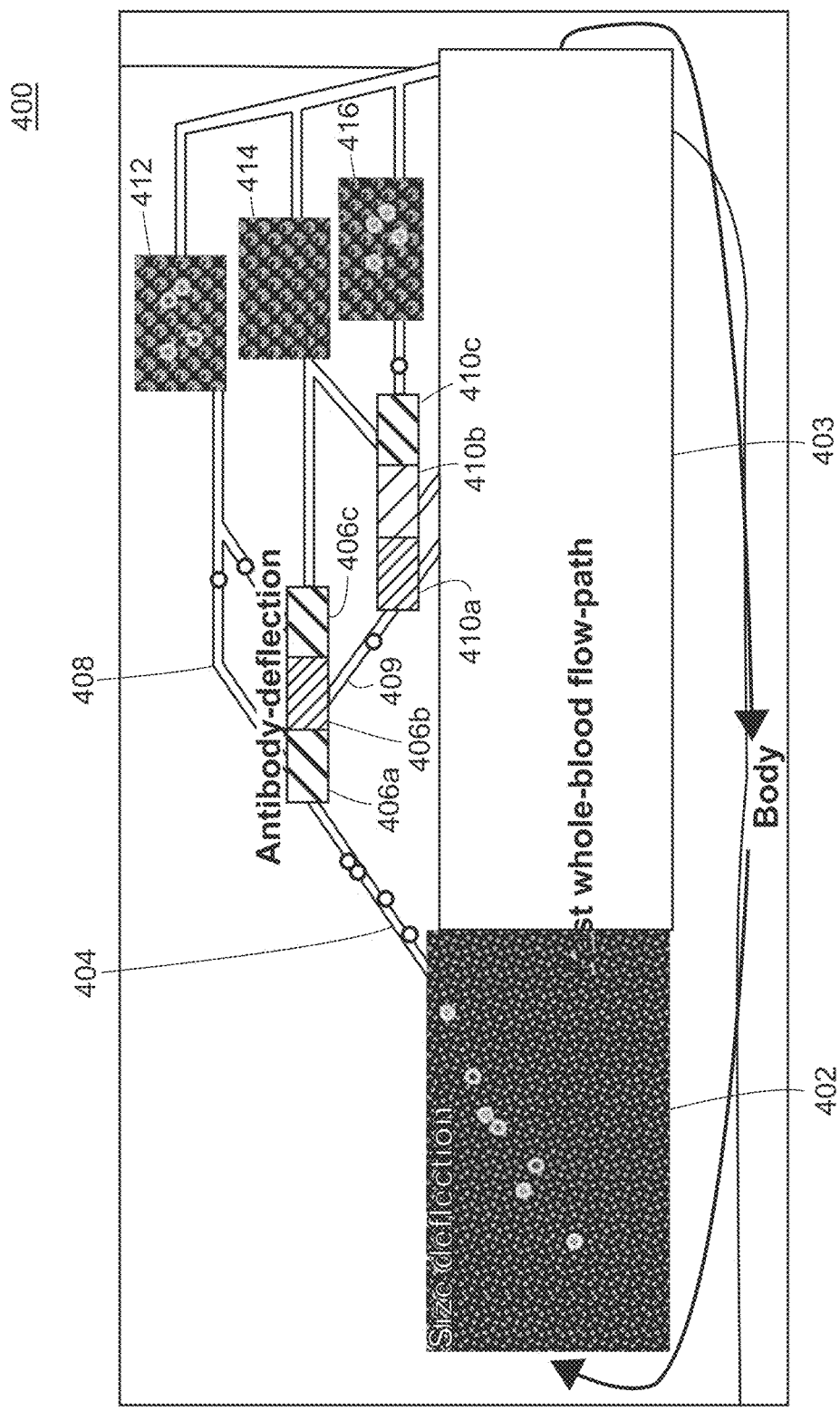
FIG. 12 is a block diagram of a multistage CTC capture device, using multiple antibody deflection regions, in accordance with an example.

The indwelling example of FIG. 11 may also be implemented using a ligand-based capture method, such as the anti-body deflection techniques discussed in reference to FIG. 12. In either implementation, indwelling devices can allow for interrogation of a larger volume blood and over a longer period of time. An indwelling device could be configured to be attached to the patient for hours, days, or longer, capturing CTCs over the entire time period, while maintaining normal blood in the patient, whether from an actively pump-assisted device, such as shown in FIG. 11 or from a passively pumped configurations relying on venous blood flow. In this way, the entire blood volume could be interrogated over a period of time. An example ligand-based capture device that may be used in an indwelling configuration is provided in FIG. 12.

FIG. 12 illustrates example implementation of a multistage cell capture device 400 that relies upon multiple antibody deflections (i.e., a ligand-based capture technique) and cell capture to identify particular cells of interest. In this way, the device 400 operates as a complex, multiple phenotype detector, which is label-free and reduces the need for further testing. The device 400 also alleviates false testing results from spontaneous cancer cell death, which can otherwise occur for some percentage of cancer cells after they leave the body. Overall, the configuration is that of a sequential combination of deviation stages, and one that may be implemented in an either an external CTC separation device or an indwelling device.

FIG. 12 illustrates an example of a binary decision tree configuration of a CTC device. The particular configuration is implemented with antibody micro-groove rolling deflection in various deflection stages, as opposed to micro-posts as in device 300. The uses multiple capture boxes for cells, each with specific combinations of properties, as identified by different antibody deflection, to collect different target cells. By way of example, targeted capture stages for any of the following combinations of antibodies and corresponding different possible cancer treatments may be used in a binary decision tree configuration:

Large AND (CD45−) AND (EpCAM+) AND (HER2+) (where the resulting cells in this stage would indicate breast cancer treatable with Herceptin)

(CD45−) AND (EpCAM+) AND (ER+) (where the resulting cells in this stage would indicate breast cancer treatable with Hormonal Therapy)

(CD45−) AND (EpCAM−) AND (CD44+) AND (CD24−) (where the resulting cells would indicate possible cancer stem cells)

(CD45−) AND (ER−) and (PR−) and (HER2−) (where the resulting combination would indicate no clear treatment)

CD45+ (white blood cells, and possibly cancer cells attached to them)

Everything else (useful for total cell count)

As shown, device 400 in FIG. 12 uses branching and re-merging channels between deflection patterns. The design avoids making all possible permutations, but rather makes the most relevant deflection/assay determinations based on downstream filter selection. As a result, for example, 5 captures stages (i.e., boxes) can be used for 8 markers instead of using 256 (2^8) boxes as would be required for all possible permutations of 8 markers.

The device 400 includes an initial antibody deflection stage 402 that, in the illustrated example, includes an anti-CD45 filter that will deviate white blood cells back into a main flow channel 403. All cells in a first CTC flow channel 404 will be CD45−, as a result. These cells will encounter a second deviation filter stage (e.g., stages 406a-406c) having a slanted pattern of microgrooves adhesive for EpCAM, which will deviate those EpCAM expressed cells into one of two channels 409 indicating positive (i.e., clean cancer epithelial cells) and channel 408 indicating negative (possible cancer stem cells).

In an example operation, cells start flowing in the device, then encounter a pattern of anti-CD45, which will deviate white blood cells back into the main flow and away from capture area. All cells that continued to flow forward are then CD45−. They will then encounter a slanted pattern of microgrooves adhesive for EpCAM, and deviate in one of two channels, channel 409 EpCAM+ (clear cancer epithelial cells) and channel 408 EpCAM− (possible cancer stem cells).

The EpCAM+ channel 409 may engage an additional deviation filter stage 410 (e.g., stages 410a-410c) having corresponding antibody-specific deviation patterns, one for each of an ER, HER2 and PR deflecting pattern. These patterns and resulting capture stages may be designed to assist medical professionals in determining the ideal treatment for a patient. While the EpCAM− channel 408 may encounter deviation stages having CD22 and CD44 antibody deflecting patterns and may be used to verify if cells are drug-resistant cancer stem cells. Capture stages 412, 414, and 416 are positioned as shown.

The device 400 is a closed, blood flow only system; and the release fluid may be maintained at a flow rate similar to that of blood flow, thereby preventing fluid backup or blood clotting at the point of re-introduction into the patient's body. In some examples, an external peristaltic-flow pump may be used to provide more control of the flow rate, especially if the flow resistance of the chip becomes too high and the blood might just mostly flow in other veins instead. A peristaltic pump acts on the tubing before or after the chip and basically squeezes and pulls up on the side of the tube at multiple points in a 1, 2, 3, 1, 2, 3, 1, 2, 3 pattern to move fluid in a single direction at a constant rate regardless of resistance.

In some examples, the deviation filter stages may be formed of micro-posts, although in the illustrated embodiment, the stages are formed from partially-adhesive line patterns, using an antibody coating, capable of deflecting cells expressed by a certain matching marker. If a cell has a marker indicating that it is "highly invasive," the cells will be deviated, otherwise the cells will continue to move in a straight line with the flow.

Once captured, cells can then be counted in each capture box without the need to use any labeling, assay, or fluorescence measurement. The presence and relative count of cells between these groups could also shed some light on heterogeneity of CTCs in patients.

Other variations include replacing the binary deviation stages with any useful deflection mechanism (size, magnetic, antibodies, etc). In this way, the present multistage techniques can be integrated into existing devices that provide deviation functionality. The integration ability of the present techniques allows for greater adaptability to existing devices. Furthermore, this ligand-based approach may be implemented in external, indwelling, and fully in vivo configurations. For the later, the CTC capture device may be placed within the vein or vessel, instead through collection and return catheters.

Further still, in some embodiments, stages can be nested together. FIG. 13A illustrates a CTC device 500 that includes an inlet region 502 leading to a main channel 504, and a nested stage 506. The nested stage 506 includes a slow down inlet end 508 that collects 10% of the laminarized fluid flow from the inlet 502. The inlet end 508 is coupled to a deviation or capture stage 510 that is coupled to a high resistance matching stage 512 formed with a switchback pattern to provide a greater resistance over a smaller surface area. The resistance stage 512 is then coupled back into the channel 504 to form an outlet region 514. In the example of FIG. 13A, the slow down stage may collect 10% of the flow and provide a 10× slow down in fluid flow into the stage 510.

FIG. 13B illustrates a CTC device 550 in which there are two nested sections: a first nested section 552 which provides a first 10× slow down in fluid flow; and a second nested section 554 with another 10× slow down, resulting in a 100× slow down overall compared to a main flow channel 556

While examples above are described as creating a laminar flow, the techniques do not require laminar flow or saline solutions. The techniques, in fact, can work with an even simpler single input of blood, if complete removal of blood cells from capture stages is not desired or if subsequent wash steps are used, an example of which is provided in FIG. 9.

In some examples, the outlets can be recombined together and/or with the main blood flow channel, for example, as used in some implementations of an indwelling device. The use of stage resistance flow-matching can allow for reintroduction without inducing detrimental flow slow down on the blood stream.

The techniques may be used with stored blood samples too, for example, through the use of external micro-pumps, such as shown in FIG. 8. The devices described herein may be implemented with or without pumping. For example, in some embodiments, a syringe may be used to inject blood flow without a flow control mechanism.

In some embodiments, the devices are used to isolate multiple different CTCs or other cells within a single operation. For example, multiple CTC channels may be arranged in series or in parallel to deviate and capture different types of CTCs, for example, based on antibody deflection or cell size. In some embodiments an initial deviation stage may equally feed numerous CTC channels each having capture stages dimensioned to capture a different CTC or cell type.

As to the types of cancers that can be examined using the cell isolation and capture, they include, but are not limited to: prostate, lung, adenocarcinoma, adenoma, adrenal cancer, basal cell carcinoma, bone cancer, brain cancer, breast cancer, bronchi cancer, cervical dysplasia, colon cancer, epidermoid carcinoma, Ewing's sarcoma, gallbladder cancer, gallstone tumor, giant cell tumor, glioblastoma multiforma, head cancer, hyperplasia, hyperplastic corneal nerve tumor, in situ carcinoma, intestinal ganglioneuroma, islet cell tumor, Kaposi's sarcoma, kidney cancer, larynx cancer, leiomyoma tumor, liver cancer, malignant carcinoid, malignant hypercalcemia, malignant melanomas, marfanoid habitus tumor, medullary carcinoma, metastatic skin carcinoma, mucosal neuromas, mycosis fungoide, neck cancer, neural tissue cancer, neuroblastoma, osteogenic sarcoma, osteosarcoma, ovarian tumor, pancreas cancer, parathyroid cancer, pheochromocytoma, primary brain tumor, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor.

The testing of devices described herein was confirmed through different techniques, including staining CTCs with DAPI for DNA content, rhodamine-conjugated anti-cytokeratin (CK) antibodies for epithelial cells, and fluorescein-conjugated anti-CD45 antibodies for hematologic cells. For example, a cell positive for cd45 is a white blood cell and therefore not a CTC. Anything without DAPI staining is not a cell; and a cell negative in cd45 and positive in ck is a CTC.

The device 300 shows a single main channel, with a height of 50-100 µm and total surface of less than 1.5 cm by 4 cm, but this pattern can be repeated, staggered, stacked, etc. to produce much higher throughput for the device. Further still, the device 300 was made with soft-lithography and PDMS for convenient rapid-prototyping, but any other material that is biocompatible and transparent will work as well. Example materials include biologically inert materials, in particular those that are amenable to micro fabrication and mass-production, including inflexible glass, fused silica and/or polystyrene. To connect the device 300 to blood, a biocompatible rubber tubing like c-flex was used.

For stages built upon a micro-post design, the width between micro-posts determines the flow characteristics in the stage, including slow down and likelihood of deviation and/or capture depending on the stage To provide resistance matching between stages, in particular the resistance stages, a series of equations were determined as follows. Initially, the Hagen-Poiseulle equation was used:

$$\Phi = \frac{dV}{dt} = v\pi R^2 = \frac{\pi R^4}{8\eta}\left(\frac{-\Delta P}{\Delta x}\right) = \frac{\pi R^4}{8\eta}\frac{|\Delta P|}{L}$$

However, because the channels have a rectangular cross-section, the pi*r^4 expression was approximated as A*(2A/P)^2, where A=Area and P=Perimeter of cross-section). From this, the following expressions were obtained:

$r=2A/P$ or $r=2*H*W/(2*(H+W))$ or $r=H*W/(H+W)$ $R=c*L/(r*r*H*W)$ or $R=c*L/(H*H*H*W*W*W/((H+W)*(H+W)))$, or $R=c*L*(H*H+W*W+2*H*W)/(H*H*H*W*W*W)$, or $R=c*L*(1/HWWW+1/HHHW+2/HHWW)$, or $R=c*L*(1/HW)*(1/WW+1/HH+2/HW)$, where H is the channel height, W is the channel width, L is the length of each path, and c is a constant.

These equations were then written for all flow paths in the design to balance resistances to appropriate ratios based on how much of the flow was to be separated at each deviation and slow-down stage. The R (resistance) values for each stage were chosen to relate to each other, so that any terms in common could be discarded, specifically the c/H since the height is the same everywhere for convenience of fabrication. The result is that R~L*(1/W³+1/WH²+2/HW²). The resistances in series are just sums, e.g., RT=R1+R2, where RT is Resistance Total, while resistances in parallel are sums of inverses, e.g., 1/RT=1/R1+1/R2. The resistances are solved so that the resistances over a first path (e.g., the blood flow channel) are equal to that of the resistances over a second path (e.g., the CTC flow channel, including any parallel sub branches thereof). That is, Rpath1=Rpath2. Finally, solving for L given W and R, the length is expressed as L=R/(1/W³+1/WH²+2/HW²) and solving for W given L and R gives 3 solutions for W, under different conditions, shown below:

$$W = \frac{L}{3H^2R} + \frac{\sqrt[3]{27H^6LR^2 + 18H^3L^2R + 3\sqrt{3}\sqrt{27H^{12}L^2R^4 + 4H^9L^3R^3} + 2L^3}}{3\sqrt[3]{2}\,H^2R} -$$

$$\left(\sqrt[3]{2}\left(-6H^3LR - L^2\right)\right) \Big/$$

$$\left(3H^2R\left(27H^6LR^2 + 18H^3L^2R + 3\sqrt{3}\sqrt{27H^{12}L^2R^4 + 4H^9L^3R^3} + 2L^3\right)^{\wedge}(1/3)\right) \text{ and } L \neq O \text{ and } HR \neq O$$

$$W = \frac{L}{3H^2R} - \frac{1}{6\sqrt[3]{2}\,H^2R}\left(1 - i\sqrt{3}\right)\left(27H^6LR^2 + 18H^3L^2R + 3\sqrt{3}\sqrt{27H^{12}L^2R^4 + 4H^9L^3R^3} + 2L^3\right)^{\wedge}(1/3) +$$

$$\left((1+i\sqrt{3})(-6H^3LR - L^2)\right) \Big/ \left(3 \times 2^{2/3} H^2R\left(27H^6LR^2 + 18H^3L^2R + 3\sqrt{3}\sqrt{27H^{12}L^2R^4 + 4H^9L^3R^3} + 2L^3\right)^{\wedge}(1/3)\right) \text{ and } L \neq O \text{ and } HR \neq O$$

$$W = \frac{L}{3H^2R} - \frac{1}{6\sqrt[3]{2}\,H^2R}\left(1 + i\sqrt{3}\right)\left(27H^6LR^2 + 18H^3L^2R + 3\sqrt{3}\sqrt{27H^{12}L^2R^4 + 4H^9L^3R^3} + 2L^3\right)^{\wedge}(1/3) +$$

$$\left((1-i\sqrt{3})(-6H^3LR - L^2)\right) \Big/$$

$$\left(3 \times 2^{2/3} H^2R\left(27H^6LR^2 + 18H^3L^2R + 3\sqrt{3}\sqrt{27H^{12}L^2R^4 + 4H^9L^3R^3} + 2L^3\right)^{\wedge}\right.$$

$$\left.(1/3)\right) \text{ and } L \neq O \text{ and } HR \neq O$$

These equations may be used in guiding the design of stages, combined with the other constraints imposed by cell size (height and width are not to be smaller than the largest cell size, plus some additional safety margin, length should not be disproportionally large for practical reasons, etc), and additional constraints and changes to flow properties added by other design features of each module (size separation and capture pillars for example change the effective W of each channel and space between then also has to be larger than the largest cell).

Figure 14:
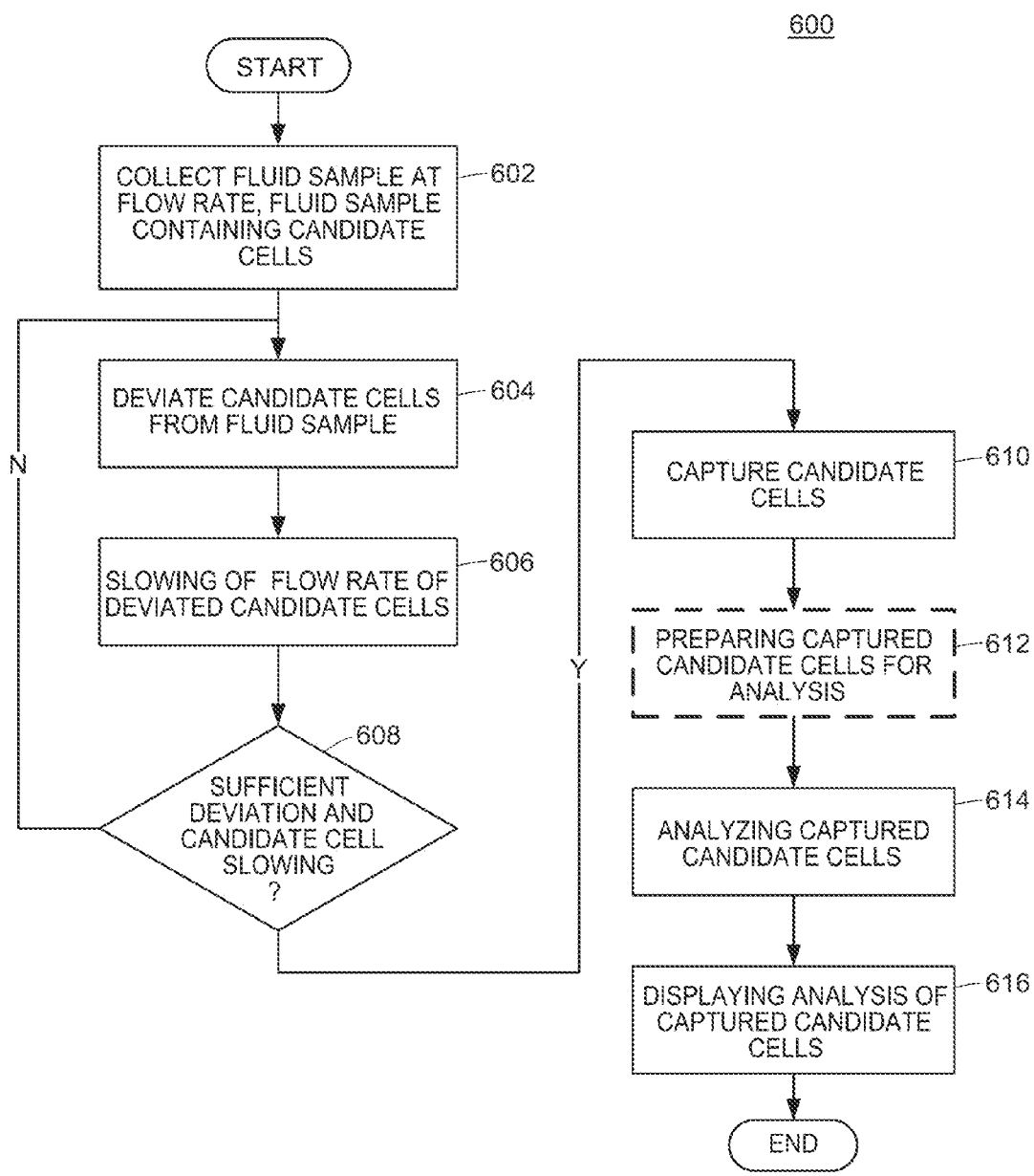
FIG. 14 is a flow diagram of a candidate cell analysis process, in accordance with an example.

FIG. 14 illustrates an example process 600 for capturing and analyzing candidate cells in a fluid sample, blood or otherwise. At a block 602, a capture device collects a fluid sample at a first flow rate, where the capture device may be an external device or an indwelling device, and where the fluid sample contains, or is believed to contain, candidate cells such as those described herein. Blocks 604 and 606 represent candidate cell deviation and flow rate slow down, respectively, that occurs in the device. While the blocks 604 and 606 are illustrated separately, they may be combined and performed together. For example, sequentially coupled stages may perform both candidate cell deflection and flow rate slowdown in each successive stage. Furthermore, the ordering of the blocks 604 and 606 is provided by way of example only, as the blocks may be implemented in any order.

In the illustrated example, a block 608 determines if there has been sufficient slowdown in fluid flow rate and sufficient deviation of candidate cells from the fluid sample or from measurement containments in the fluid sample. If not, then, as represented in the illustrated example, blocks 604 and 606 perform further deviation and flow slowdown. This loop control may represent a different number of stages as shown in FIGS. 1A, 2 and 3, for example. If sufficient deviation and slowdown has occurred, then the candidate cells are captured at a block 610. After cell capture, control is passed to an optional block 612 for captured cell preparation. In other examples, the blocks 604, 606, and 610 may be performed by the same stage and not separated, from which the block 608 would operate to determine if additional stages would be needed. The block 608 could be manually determined by a device designer or could be determined during operation. Preparation at block 612 may involve taking the captured candidate cells and suspending them in a pipette used for separation. In other examples, the device itself, e.g., implemented as a lab-on-a-chip design, could be mounted to or with a cartridge used by analyzer system, such as a fluorescence spectroscopy/microscopy system at block 614. The block 614 may represent any number of candidate cell analysis systems, including any one or more of an optical analysis, visual inspection, automated counting, microscopy, magnetic detection, or electrical detection. The analyzed data may be then be displayed to a patient or care provider and/or data-based for future reference purposes at a block 616.

Figure 15:
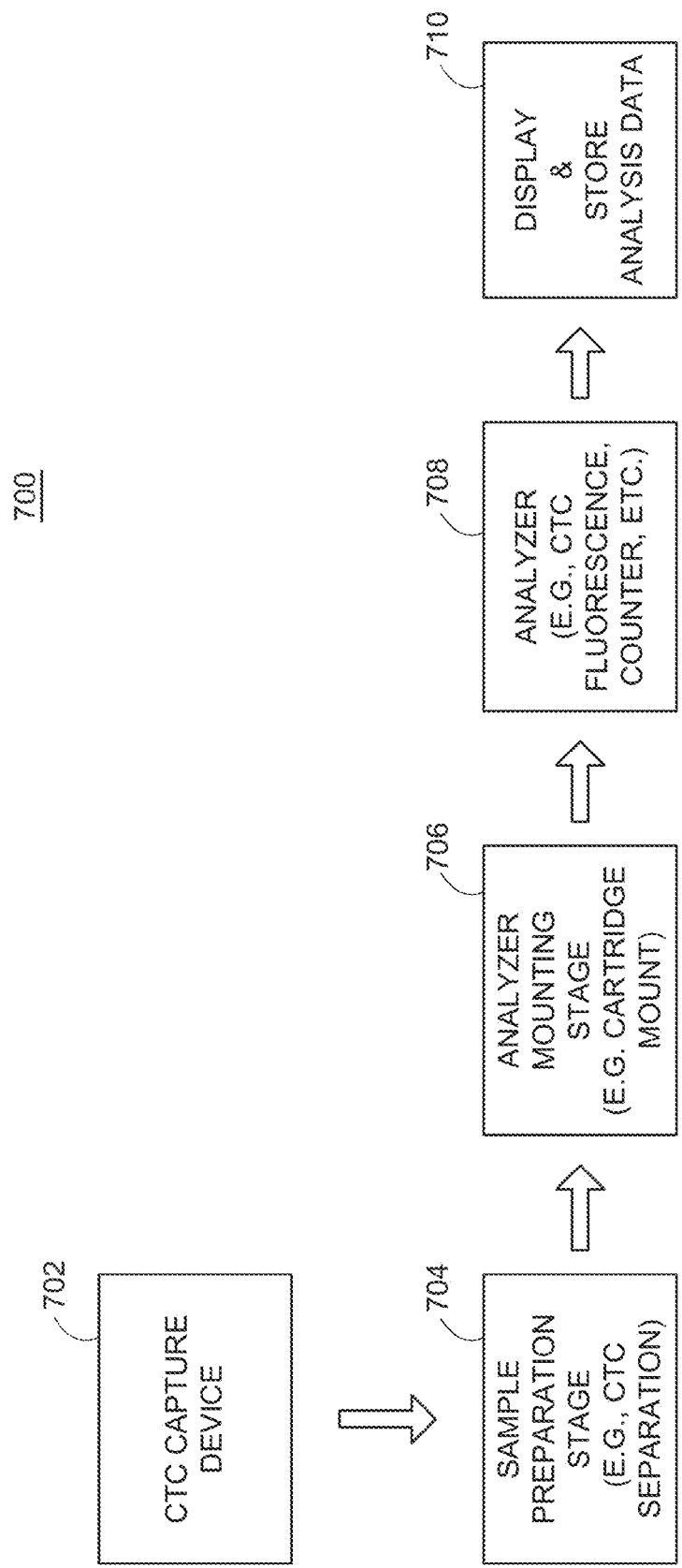
FIG. 15 is a block diagram of a candidate cell analysis system, in accordance with an example.

FIG. 15 illustrates a candidate cell analysis system 700 in accordance with an example. A candidate cell capture device 702, such as the CTC capture devices in FIGS. 2 and 3, captures cells for analysis. The cells may provided to an optional sample preparation stage 704, e.g., for staining CTCs and/or placing them into solution in a pipette and performing a plasma separation. This stage may be optional in that the capture 702 device is able to isolate CTCs with high selective/specificity, over traditional CTC measurement techniques, meaning isolation after staining may not be needed depending on the analysis type. Therefore, this sample preparation stage 704 may be implemented with conventional CTC measurement systems or where desired to transfer the CTCs into another fluid sample medium. In any event, a mounting stage 706 is used to mount the captured CTCs from the device 702 into an analyzer. The device 702 may be made with capture stages directly compatible with existing cartridge mounts, for example, while in other examples the device 702 may function at a mountable cartridge. An analyzer 708 analyzes the captured CTCs for display and stage at a display and memory storage, respectively, represented by stage 710. The analyzer may be an optical analyzer, automated counting system, microscopy system, magnetic detection system, or electrical detection system. The analyzer may include a cell detection readout circuit made of a pixel sensor array that examines the captured CTC continuously or periodically.

In other examples, the analyzer 708 may include multiple CTC detectors, such as multiple cell detection readout circuits, each positioned at different stages of the device 702 to analyze captured CTC cells during runtime.

The various blocks, operations, and techniques described above may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any computer readable memory such as on a magnetic disk, an optical disk, or other storage medium, in a RAM or ROM or flash memory of a computer, processor, hard disk drive, optical disk drive, tape drive, etc. Likewise, the software may be delivered to a user or a system via any known or desired delivery method including, for example, on a computer readable disk or other transportable computer storage mechanism or via communication media. Communication media typically embodies computer readable instructions, data structures, program modules or other data in a modulated data signal such as a carrier wave or other transport mechanism. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Thus, the software may be delivered to a user or a system via a communication channel such as a telephone line, a DSL line, a cable television line, a wireless communication channel, the Internet, etc. (which are viewed as being the same as or interchangeable with providing such software via a transportable storage medium).

Moreover, while the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

What is claimed is:

1. A device for separating candidate cells from a carrier fluid, the device comprising:
    a separation channel to receive the carrier fluid having a first flow rate and to provide for an isolation fluid, wherein the separation channel is configured to deflect the candidate cells from the carrier fluid into the isolation fluid; and
    a capture stage coupled to the separation channel through a coupling stage, wherein the coupling stage comprises a plurality of progressive slow down stages each configured to reduce the flow rate of the incident isolation fluid and deflected candidate cells received by the respective slow down stage, and wherein the capture stage is configured to capture the deflected candidate cells over a sampling period.

2. The device of claim 1, wherein the separation channel maintains a laminar flow of the carrier fluid and the isolation fluid.

3. The device of claim 1, wherein the separation channel is a deviation channel comprising a micro-post pattern dimensioned to deviate the candidate cells based on cell size.

4. The device of claim 1, wherein the separation channel is a deviation channel comprising a micro-post pattern dimensioned to deviate the candidate cells from the remaining cells in the carrier fluid.

5. The device of claim 1, wherein the first flow rate is at or below a normal blood flow rate for a patient.

6. The device of claim 1, wherein the separation channel is a deviation channel that deviates only candidate cells into the isolation fluid.

7. The device of claim 1, wherein the separation channel propagates the carrier fluid at the first flow rate from an inlet to the separation channel to an outlet from the separation channel.

8. The device of claim 1, wherein the separation channel is a deviation channel that deflects the candidate cells based on antibody deflection created in the deviation channel using patterned angled lines on opposing channel walls of the deviation channel, where the patterned angled lines are chosen to deviate the candidate cells by transient adhesion to included antibodies, thereby slowing down the candidate cells and deflecting the candidate cells at an angle.

9. The device of claim 1, wherein the capture stage comprises a micro-post pattern dimensioned to capture the candidate cells.

10. The device of claim 1, wherein the separation stage has a first outlet for egressing the carrier fluid at the first flow rate and a second outlet for egressing the isolation fluid and deviated candidate cells at the first flow rate.

11. The device of claim 10, wherein the coupling stage is coupled to the second outlet, such that a first of the plurality of slow down stages reduces the flow rate of the isolation fluid and deviated candidate from the first flow rate to a second flow rate less than the first flow rate.

12. The device of claim 11, wherein the second flow rate is at least 10× slower than the first flow rate.

13. The device of claim 11, where the coupling stage comprises:
   the first slow down stage coupled to the second output and configured to slow down the flow rate of the isolation fluid and deviated candidate cells from the first flow rate to a second flow rate lower than the first flow rate; and
   a second separation stage coupled to the first slow down stage to further deviate the candidate cells, the second separation stage having a third outlet supporting flow at the second flow rate and a fourth outlet supporting flow at a third flow rate lower than the second flow rate.

14. The device of claim 1, wherein the carrier fluid is blood and the candidate cells are circulating tumor cells.

15. The device of claim 1, wherein the carrier fluid is blood and the candidate cells are cancer cells.

16. The device of claim 15, wherein the cancer cells are epithelial cells, endothelial cells, neurons, hepatocytes, nephrons, glial cells, muscle cells, skin cells, adipcytes, fibroblasts, chondrocytes, osteocytes, or osteoblasts.

17. The device of claim 15, where the cancer cells express at least one marker of prostate cancer, lung cancer, adenocarcinoma, adenoma, adrenal cancer, basal cell carcinoma, bone cancer, brain cancer, breast cancer, bronchi cancer, cervical dysplasia, colon cancer, epidermoid carcinoma, Ewing's sarcoma, gallbladder cancer, gallstone tumor, giant cell tumor, glioblastoma multiforma, head cancer, hyperplasia, hyperplastic corneal nerve tumor, in situ carcinoma, intestinal ganglioneuroma, islet cell tumor, Kaposi's sarcoma, kidney cancer, larynx cancer, leiomyoma tumor, liver cancer, malignant carcinoid, malignant hypercalcemia, malignant melanomas, marfanoid habitus tumor, medullary carcinoma, metastatic skin carcinoma, mucosal neuromas, mycosis fungoide, neck cancer, neural tissue cancer, neuroblastoma, osteogenic sarcoma, osteosarcoma, ovarian tumor, pancreas cancer, parathyroid cancer, pheochromocytoma, primary brain tumor, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor.

18. The device of claim 1, wherein the capture stage is to allow cell growth of the deviated candidate cells.

19. The device of claim 1, wherein the carrier fluid is blood, the device further comprises:
   an extraction stage to collect the blood from a blood-vessel of a patient, the blood having a normal blood flow rate for the patient, into the separation channel; and
   an insertion stage to re-introduce the blood into the vessel after deviation of the candidate cells, where the blood is re-introduced substantially at or up to the first flow rate.

20. The device of claim 1, wherein the carrier fluid is blood and the isolation fluid is a water solution, a saline solution, or a water and saline solution.

21. The device of claim 1, wherein the separation channel is configured to deflect at least 90% of the candidate cells in the carrier fluid into the isolation fluid.

22. The device of claim 1, wherein each of the plurality of slow down stages is configured to reduce flow rate by the same reduction factor.

23. The device of claim 1, wherein the reduction factor is 10×.

24. The device of claim 1, wherein the first flow rate is between 1 ml/min and 10 ml/min.

25. A method of analyzing candidate cells captured in the capture stage of the device of claim 1, the method comprising applying at least one of an optical analysis, visual inspection, automated counting, microscopy, magnetic detection, or electrical detection to at least some of the captured candidate cells.

* * * * *

UNITED STATES PATENT AND TRADEMARK OFFICE
CERTIFICATE OF CORRECTION

PATENT NO. : 8,951,484 B2  
APPLICATION NO. : 13/756121  
DATED : February 10, 2015  
INVENTOR(S) : Tommaso F. Bersano-Begey et al.

Page 1 of 1

It is certified that error appears in the above-identified patent and that said Letters Patent is hereby corrected as shown below:

In the specification

At Column 7, line 25, "adipcytes," should be -- adipocytes, --.

At Column 15, line 29, "veticulum" should be -- reticulum --.

In the claims

At Column 20, line 3, "adipcytes," should be -- adipocytes, --.

At Column 20, line 24, "veticulum" should be -- reticulum --.

Signed and Sealed this  
Twenty-ninth Day of December, 2015

Michelle K. Lee  
*Director of the United States Patent and Trademark Office*